United States Patent
Barrett et al.

(10) Patent No.: US 11,342,057 B2
(45) Date of Patent: May 24, 2022

(54) DYNAMIC GRAPHICAL USER INTERFACE FOR INTERACTION WITH PATIENT RESPIRATORY DISEASE DATA

(71) Applicant: Reciprocal Labs Corporation, Madison, WI (US)

(72) Inventors: Meredith A. Barrett, Redwood City, CA (US); Mike Lohmeier, Sun Prairie, WI (US); Shannon M. Hamilton, Berkeley, CA (US); Michael J Tuffli, Kentfield, CA (US); Dmitry Stupakov, Cupertino, CA (US); Christopher Hogg, San Francisco, CA (US); John David Van Sickle, Oregon, WI (US)

(73) Assignee: Reciprocal Labs Corporation, Madison, WI (US)

( * ) Notice: Subject to any disclaimer, the term of this patent is extended or adjusted under 35 U.S.C. 154(b) by 804 days.

(21) Appl. No.: 15/847,382

(22) Filed: Dec. 19, 2017

(65) Prior Publication Data
US 2019/0189258 A1    Jun. 20, 2019

(51) Int. Cl.
| | |
|---|---|
| *G16H 20/10* | (2018.01) |
| *A61M 15/00* | (2006.01) |
| *G16H 10/60* | (2018.01) |
| *G16H 20/13* | (2018.01) |
| *G06Q 10/10* | (2012.01) |
| *G16H 40/63* | (2018.01) |

(52) U.S. Cl.
CPC .......... *G16H 20/10* (2018.01); *A61M 15/008* (2014.02); *G16H 10/60* (2018.01); *G16H 20/13* (2018.01); *A61M 2205/502* (2013.01); *G06Q 10/1093* (2013.01); *G16H 40/63* (2018.01)

(58) Field of Classification Search
CPC ...................................................... G16H 20/10
See application file for complete search history.

(56) References Cited

U.S. PATENT DOCUMENTS

| | | | |
|---|---|---|---|
| 10,019,555 B2 * | 7/2018 | Manice | ................. G09B 19/00 |
| 2002/0116226 A1 | 8/2002 | Auer et al. | |
| 2013/0066655 A1 | 3/2013 | Naeymi-Rad et al. | |
| 2014/0129249 A1 | 5/2014 | Nkoy et al. | |

(Continued)

FOREIGN PATENT DOCUMENTS

| | | |
|---|---|---|
| WO | WO 2016/172614 A1 | 10/2016 |
| WO | WO 2017/032873 A2 | 3/2017 |

OTHER PUBLICATIONS https://web.archive.org/web/20180624141723/https://www.caretrx.com/ (Year: 2018).*

(Continued)

*Primary Examiner* — Robert A Sorey
*Assistant Examiner* — Kristine K Rapillo
(74) *Attorney, Agent, or Firm* — Fenwick & West LLP

(57) ABSTRACT

This description relates to insight into the asthma management habits of a patient or a plurality of patients. The provided information includes records of rescue medication usage events, records of controller medication events, and overall evaluations of a patients disease management. Users of the application may include both patients who may use the information to monitor their own habits or providers who may use the information to monitor patients or improve a patient's existing medication regimen.

21 Claims, 23 Drawing Sheets

Analytics System
100

(56) References Cited

U.S. PATENT DOCUMENTS

| | | | |
|---|---|---|---|
| 2015/0100335 A1* | 4/2015 | Englehard | A61M 15/008 |
| | | | 705/2 |
| 2015/0112707 A1 | 4/2015 | Manice et al. | |
| 2015/0150484 A1 | 6/2015 | Wekell | |
| 2015/0269348 A1* | 9/2015 | Madjd | G16H 40/67 |
| | | | 705/3 |
| 2015/0332012 A1* | 11/2015 | Edelson | A61B 5/7275 |
| | | | 705/2 |
| 2015/0379233 A1* | 12/2015 | Aysseh | G06Q 30/0205 |
| | | | 705/3 |
| 2017/0109493 A1 | 4/2017 | Hogg et al. | |

OTHER PUBLICATIONS

McDonald, C.J. et al., "The Medical Gopher—a microcomputer system to help find, organize and decide about patient data," Western Journal of Medicine, Dec. 1986, vol. 145, No. 6, pp. 823-829.

PCT International Search Report and Written Opinion, PCT Application No. PCT/US2018/064979, dated Mar. 11, 2019, 14 pages.

European Patent Office, Extended European Search Report and Opinion, EP Patent Application No. 18891327.1, dated Aug. 26, 2021, 11 pages.

\* cited by examiner

| PATIENT TYPE | PATIENT Name | Asthma Control last 7 days | Rescue Use ↓ last 7 days | Adherence last 7 days | Last Sync with Rescue Sensor | Last Contact with Care Team |
|---|---|---|---|---|---|---|
| Asthma | RAMIREZ, Jayden | Very Poor | ① ② ③ ④ ⑤ ⑥ 16 | 64% | 13 Apr 2017 | 13 Apr 2017 |
| COPD | AUSTIN, Benjamin | Not Well | ① ② ② ③ ③ ⓣ 13 | 14% | 13 Apr 2017 | N/A |
| Sensor Inactive | CHAVEZ, Dylan | Not Well | ① ① ① Ⓜ ② ⓣ 7 | 42% | 12 Apr 2017 | N/A |
| | CLARK, Julian | Not Well | Ⓕ Ⓢ ⑤ Ⓜ Ⓦ ⓣ 5 | 157% | 13 Apr 2017 | N/A |
| | POWELL, Anthony | Well | Ⓕ Ⓢ Ⓢ Ⓜ ① ⓣ 2 | 64% | 13 Apr 2017 | N/A |
| | ANDREWS, Ethan | Well | Ⓕ Ⓢ Ⓢ Ⓜ ① ⓣ 2 | 5% | 13 Apr 2017 | N/A |
| | MARSHALL, Tyler | Well | Ⓕ Ⓢ Ⓢ Ⓜ ① ⓣ 1 | 8% | 12 Apr 2017 | N/A |
| | WHITE, John | Well | Ⓕ Ⓢ Ⓢ Ⓜ ① ⓣ 1 | N/A | 12 Apr 2017 | N/A |

| PATIENT TYPE | PATIENT ⊙ Name | Rescue Baseline last 30 → 24 hrs | Rescue Use ↓ last 7 days | Adherence last 7 days | Last Sync with Rescue Sensor | Last Contact with Care Team |
|---|---|---|---|---|---|---|
| Asthma | | | | | | |
| MOORE, Anthony | 1.38 → 0 | ③③②③⑤③ Ⓕ24 | 75% ▬▬▬▭ | 13 Apr 2017 | N/A 13 Apr 2017 |
| COPD Sensor Inactive | MORALES, Caleb | 1.03 → 0 | ⑥④④③③③ Ⓕ24 | 75% ▬▬▬▭ | 13 Apr 2017 | N/A |

Control Medication Events
03 Jul 2017 – 09 Jul 2017

∨ PATIENT SENSOR INFO & SCHEDULE (AS OF 19 JUL 2017)

AeroBid (Controller)
Sensor ID: B4:A5:2E
Sync To: Motorola Moto X (Android)
Last Sync:19 Jul 2017
Last Bluetooth Status: On
Puffs per Dose: 1
Dose Schedule: 9:00 am | 5:00 pm 407a

| | | | |
|---|---|---|---|
| Monday, 03 Jul 2017 | | | |
| 9:51 AM | AeroBid | 1 Puff | |
| 11:51 AM | AeroBid | 1 Puff | 2/2 Taken |
| Tuesday, 04 Jul 2017 | | | |
| 1:51 PM | AeroBid | 1 Puff | 1/2 Taken |
| Wednesday, 05 Jul 2017 | | | 0/2 Taken |
| Thursday, 06 Jul 2017 | | | |
| 11:51 AM | AeroBid | 1 Puff | 2/2 Taken |
| Friday, 07 Jul 2017 | | | |
| 4:51 PM | AeroBid | 1 Puff | 1/2 Taken |

At Risk

510ee

You just used the rescue medication again 3 times in the last 24 hours, which is 30% more than usual.

Quiet Sensor

510ff

We have not heard from your Dulera sensor in over 48 hours. Regular sensor syncing will help Propeller manage your condition.

Oh no!

510gg

We haven't recorded your 9:00 AM dose of Dulera. Don't forget to take it!

DYNAMIC GRAPHICAL USER INTERFACE FOR INTERACTION WITH PATIENT RESPIRATORY DISEASE DATA

BACKGROUND

Field of Art

The disclosure relates generally to graphical user interfaces for display on computing devices, and more specifically to graphical user interfaces for healthcare providers viewing patient data.

Description of the Related Art

Medicament devices such as inhalers allow patients to manage respiratory symptoms such as constricted airflow. Many respiratory disease patients, such as sufferers of asthma, chronic obstructive pulmonary disorder (COPD), and cystic fibrosis, have symptoms that are related to environmental triggers and factors such as air quality, weather, land use, and the like. A particular patient or group of patients may have sensitivities to multiple triggers and factors. Knowing which of dozens, hundreds, or more triggers and factors a patient is sensitive to and monitoring those triggers and factors for use in managing symptoms is a complex task and is not currently feasible for many patients and providers.

Further, each individual respiratory disease is on its own a significant and costly public health problem. Taking asthma as just one example, the World Health Organization estimates the worldwide population with asthma may be 300 million, and predicts that it will rise to 400 million by 2025. In the United States, asthma affects 1 in 12 individuals in the U.S. and prevalence is on the rise, leading to more than $56 billion per year in health care utilization costs. Despite the development of new medications, rates of hospitalizations and emergency room visits have not declined. Each year in the United States the disease causes approximately 2 million emergency department visits, 500,000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments, however, only 1 in 5 asthmatics has the disease under control. Newly revised national guidelines urge doctors to more closely monitor whether treatment is controlling everyday symptoms and improving quality of life.

Physicians, however, have few available tools to assess how well their patients are doing day-to-day. An increasing number of physicians have begun to use periodic, written questionnaires (such as the Asthma Control Test (ACT)) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used. More generally, patient assessment and monitoring is difficult if used at all other respiratory diseases as well.

SUMMARY

A respiratory disease analytics system is a unified platform for treating, monitoring, and managing the respiratory diseases of a number of patients. Examples of such diseases include, but are not limited to, asthma, COPD, and cystic fibrosis. The analytics system tracks respiratory rescue and controller medication events by receiving event notifications from a sensor attached to a medicament device (e.g., inhaler) used by a patient who has authorized the analytics system to help manage their disease. The sensor, when attached to or incorporated in a metered dose inhaler or other medicament device, records the time and date of the usage event, and communicates that information to the analytics system. The analytics system analyzes the received events (both the most recent and previously received events) in real time or near-real time, and is capable of delivering risk assessments, controller adherence reminders, and other information to guide and manage the disease in the form of notifications to patients and their healthcare providers.

The displayed graphical user interface allows users, such as patients and medical providers, to easily monitor the disease management habits of a single person or a group of people suffering from a variety of diseases and medical conditions. When used by medical provides, the application generates different displays of the graphical user interface responsive to inputs from the user detailing general patient overviews and more specific patient medicament details such as adherence habits and records of rescue usage events. For patient users, the application displays a variety of notifications ranging from risk analyses to disease management suggestions.

The disease analytics system relieves existing concerns associated with patient monitoring by removing the user bias associated with written questionnaires. Instead the system of sensors automatically record and highlight relevant information to assess the amount of danger a patient is in and gauge their rescue medication habits. Additionally, communication between a provider and a patient is not dependent the patient scheduling an appointment since the system allows the provider immediate insight into the patients daily medication habits and risk events.

BRIEF DESCRIPTION OF DRAWINGS

FIG. 4A-4G represent graphical elements of a graphical user interface presented on the display of a computing device associated with care providers, according to one embodiment.

FIG. 5A-5M represent graphical elements of a graphical user interface presented on the display of a computing device associated with patients, according to one embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
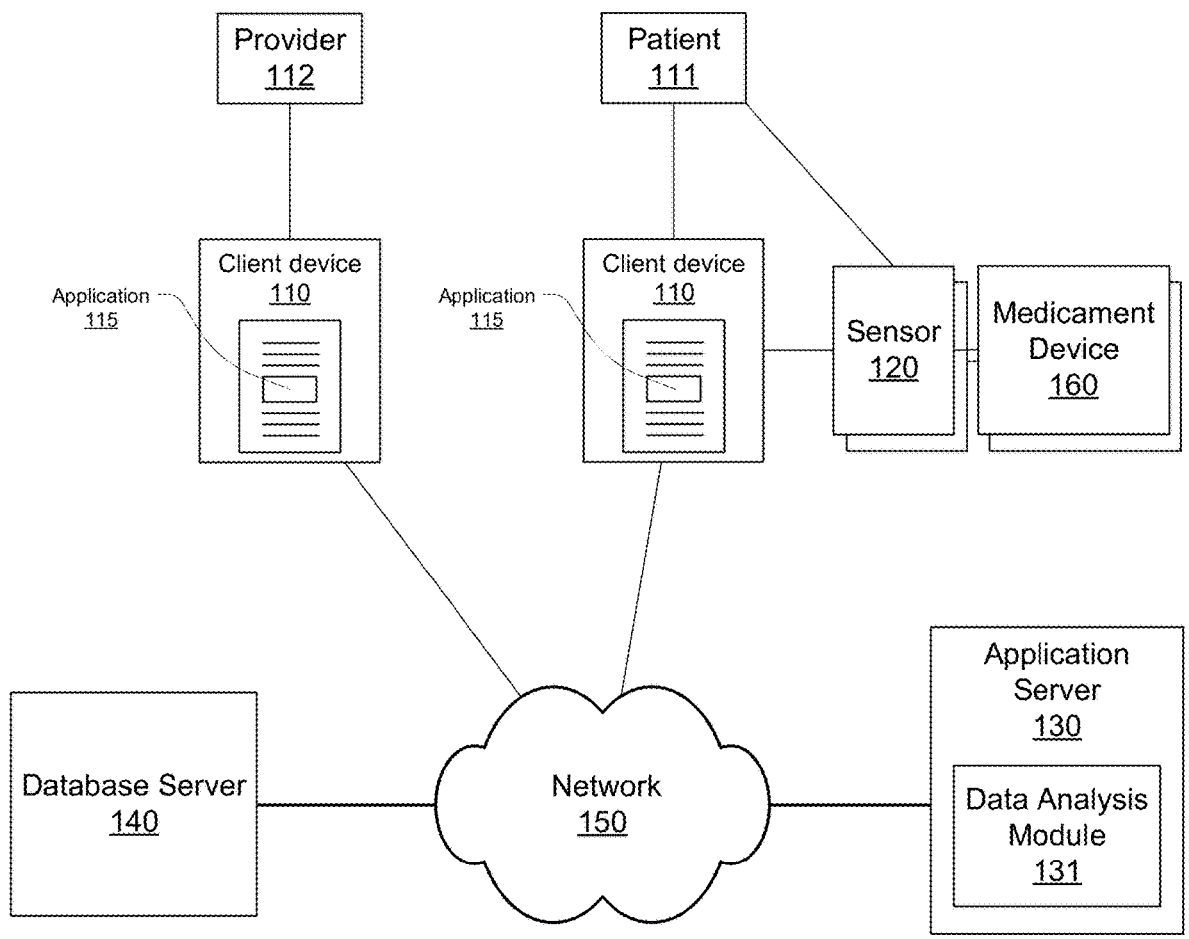
FIG. 1 shows an analytics system for monitoring accurate, real-time medicament device usage, performing analytics on that data, and providing asthma rescue event risk notifications, according to one embodiment.

FIG. 1 shows an analytics system 100 for monitoring accurate, real-time medicament device events, performing analytics on that data, and presenting the analytics to a user through a graphical user interface, according to one embodiment.

The analytics system includes client computing devices 110, a medicament device sensor 120, a medicament device 160, an application server 130, database server 140, and a network 150. Although FIG. 1 illustrates only a single instance of most of the components of the analytics system 100, in practice more than one of each component may be present, and additional or fewer components may be used.

I.A. Client Device and Application

The client devices 110, at the behest of their users, interact with the analytics system 100 via the network 150. For purposes of explanation and clarity it is useful to identify at least two different types of users. A patient 111 is a user burdened with a respiratory disease who makes use of the analytics system 100 at least in part to obtain information about management and tracking of their disease from the server 130. Generally, to enable this information exchange the user grants the analytics system 100 permission to monitor the patient's 111 medicament device 160 usage. As will be explained below, medication events are detected by a sensor 120 associated with the medicament device 160 and the user's client device 100, which in turn reports to the application server 130, which in turn can provide information back to the patient. In one example process, the server 130 generates notifications which are provided to the patient through an associated client device 110.

Another type of user is a healthcare provider 112 who, again with the patient's 111 express permission, also receives information regarding their patient's respiratory disease management. This information may include both individual patient data as well as aggregated medication usage event data reported by the sensors 120, as well external data and derived statistics regarding any combination of these different types of data. Often, the provider 112 will be the primary care physician of a number of the patients 111 and/or a specialist physician to the patients 111. Other types of users are also contemplated, such as parents/ guardians of patients 111 who may also want to report information in the event that their own client devices 110 are distinct from those of their children.

The client device 110 is a computer system. An example physical implementation is described more completely below with respect to FIG. 2. The client device 110 is configured to wirelessly communicate with the analytics system 100 via network 150. With network 150 access, the client device 110 transmits to system 100 the user's geographical location and the time of a medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the analytics system 100 may also exchange information with other connected client devices 110. For example, through a client software application 115, a healthcare provider 112 may be provided a graphical user interface that provides information about the disease state of one or more patients 111. The healthcare provider 112 may react to that information and use the application 115 to send a recommendation to the patient 111 for treatment or adjustment of behavior to improve disease management. Similarly, through application 115 patients 111 may communicate with their health care providers 112 and, permission depending, other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the analytics system 100. For example, the dashboard allows patients 111 and providers 112 to interact with each other, view notifications, exchange messages about treatments and treatment regimens, provide and receive event and all other non-event data, and so on. Application 115 may be coded as a web page, series of web pages, or content otherwise coded to render within an internet browser. Application 115 may also be coded as a proprietary application configured to operate on the native operating system of the client device 110. An example dashboard is more completely described below in conjunction with FIG. 3. Embodiments of a healthcare provider specific dashboard are described below in conjunction with FIG. 4.

In addition to providing the dashboard, application 115 may also perform data processing on event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicate information relating to medicament device usage with the client device 110. If the sensor 120 hasn't been paired with a client device 110 prior to an event, the information is stored locally until such a pairing occurs. Upon pairing, the sensor 120 communicates any stored event records to the client device 110. In other implementations, other types of wireless connections are used (e.g., infrared or 802.11).

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audio-visual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient 111 may be associated with more than one medicament device 160. For example, the patient 111 may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time and geographical location of the medication event, that is, usages of the rescue medicament device 160, by the patient 111. Each sensor 120 transmits the event data in real-time or as soon as a network connection is achieved, automatically without input from the patient 111 or health care provider 112. The medication event information is sent to the application server 130 for use in analysis, presentation of a dashboard to the healthcare provider, generation of notifications, and other purposes.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are generally not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
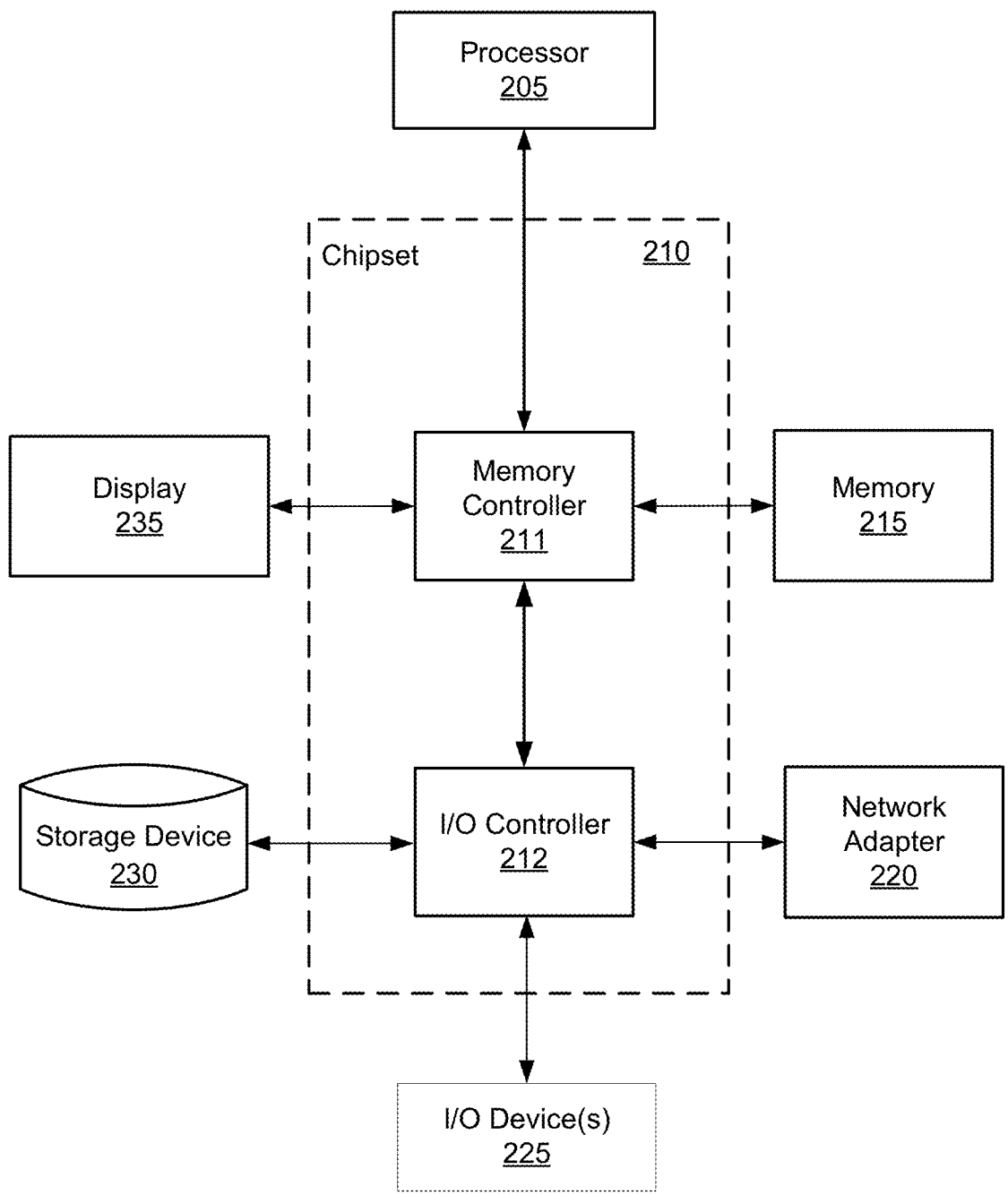
FIG. 2 is a high-level block diagram illustrating an example of a computing device used in either a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160, including both rescue medication and controller medication events, collaborate on asthma treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the analytics system 100. The patient profile may include identifying information about the patient such as age, gender, disease type, account creation date, proxy device, current rescue medication, current controller medication, notification preferences, a controller medication adherence plan, a patients relevant medical history, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives medication event information from the client device 110 or the sensor 120, triggering a variety of routines on the application server 130.

In the example implementations described below, the data analysis module 131 executes routines to access event data as well as other data including a patient's profile, analyze the data, and output the results of its analysis to both patients 111 and providers 112. These analyses may be performed at any point in time, in response to a rescue event particularly, due to a relevant change in the patient's environment, in response to a request of presentation of a dashboard to a healthcare provider on their client device, and in response to any one of a number of triggering conditions discussed further below.

Many types of analyses are possible. Examples include asthma, COPD, or other respiratory disease risk analyses, where the risk may, for example, be the risk of a future attack or other compromising event. As another example, a risk analysis may be performed using rescue and controller medication event data for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers information to send to patients 111, authorized healthcare providers 112, and/or other users provided access to the patient's profile. The information may presented in the form of a dashboard such as a user interface designed for use by a healthcare provider (herein referred to as a provider GUI), as well as in the form of push notifications presented as part of a dashboard on a client device. The notifications and provider GUI can provide details about the timing, location, and affected patient(s) 111 involved in a medication rescue event, they may include a distress or emergency signal that requests emergency assistance. They may also include the results of an analysis performed by the data analysis module 131. More information regarding types of notifications specifically that may be sent and the content they may contain is further described below in reference to FIG. 5A-5M.

In addition to providing push notifications in response to a risk analysis, notifications may also be provided as pull notifications, at particular time intervals. Additionally, some notifications (whether push or pull) may be triggered not in response to a risk analysis performed in response to a rescue medication event, but instead in response to a risk analysis performed in response to one of the underlying factors in the risk analysis changing, such that an updated notification is warranted. For example, if weather conditions indicate that an increase in air pollution is occurring or is imminent, this may trigger the carrying out of a risk analysis for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider data related data such as profiles, medication events, and patient medical histories (e.g., electronic medical records). Patient and provider data is encrypted for security and is at least password protected and otherwise secured to meet all Health Insurance Portability and Accountability Act (HIPAA) requirements. Any analyses (e.g., an asthma risk analysis) that incorporate data from multiple patients (e.g., aggregate rescue medication event data) and are provided to users is de-identified so that personally identifying information is removed to protect patient privacy.

The database server 140 also stores non-patient data. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, the air quality index, and so on. Another example is geo-referenced pollution data, including particulate counts for various pollutants at an instance of time or measured empirically. The regional data includes information about the current weather conditions for the time and place of the rescue event such as temperature, humidity, air quality index. All of the items of data above may vary over time, and as such the data itself may be indexed by time, for example separate data points may be available by time of day (including by minute or hour), or over longer periods such as by day, week, month, or season.

Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3:
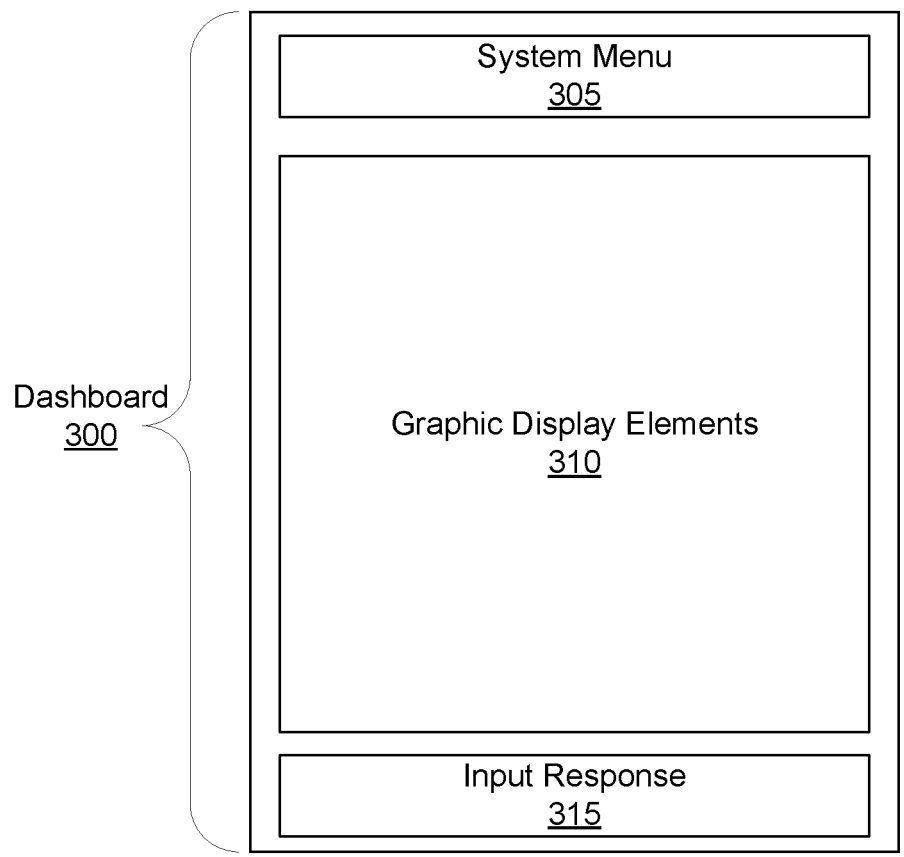
FIG. 3 shows a dashboard of a client application that allows a user to interact with an analytics system, according to one embodiment.

The dashboard, for example dashboard 300 illustrated in FIG. 3, allows users to interact with the analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and receive notifications. In one implementation, patients may not communicate with other health care providers and other patients through the dashboard 300. In alternate implementations such communication is enabled, for example, to discuss and share information about their disease, medication usage, and disease management. The ability to share healthcare information may give patients or healthcare care providers experiencing a same issue a way to share individual perspectives.

The dashboard 300 also allows authorized health care providers 112 to access a list of patients to view, annotate, update, interact with, and export information about patient and community data and statistics in various demographics or geographic segments. Using the dashboard 300, healthcare providers are able to monitor patients individually or in aggregate, to receive and provide feedback (e.g. compliance reminders) on how their associated patient populations are responding to management guidance. A healthcare provider who has access to individual or multiple patients has the ability to establish notification thresholds, set parameters for the notifications, and receive notifications when patients' event history matches certain conditions (e.g., in response to a patient having a rescue event). Additionally, the dashboard 300 can receive and display regular reports of event patterns for specific demographic generated by the analytics system 100.

The dashboard 300 presents a variety of information including tabular data, graphical visualizations, and analyses to users through different graphical display elements 310 that form part of the graphical user interface. To interact with information presented, some display elements 310a include an input response 315 area. For example, in the display element 310b illustrated in FIG. 5A, a patient may scroll up or down in the input response 315 area to select a controller medication used to manage asthma or select the "next" to move to an additional display element 310.

In some instances, these elements are referred to as "cards", typically for information presented to the patients. Often cards are specifically suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information. Other implementations of the dashboard 300 may be specifically suited for consumption on larger displays typical of desktop or laptop computing devices. In these dashboards 300, there are typically multiple different display elements on visible on the screen simultaneously. The presentation, position, and interaction of these various display elements for the provider UI specifically is described below with respect to FIG. 4.

For notifications specifically, notifications include not only information to be presented to the user through the application 115, but also parameters for specifying which display element 310 is to be used to display the contents of the notification. Generally, any information pushed/pulled from the application server 130 may be associated with one or more cards. For example, a notification can be pushed to the patient based on the outcome of a risk analysis. The dashboard 300 will process the notification and determine which card/s to use to present the information in the notification. Continuing the example, the recipient of the notification may make a request (pull) data from the application server 130. The application server 130 provides the requested data in another notification, and the dashboard 300 then determines which display card 310 to display the requested information.

IV. Provider Side Graphics Display

IV.A. Overview

The provider GUI/provider dashboard 300 graphically presents a variety of information to healthcare providers 112 using interactive graphical elements. The following section describes a number of possible graphical elements in conjunction with the example display elements illustrated in FIG. 5.

Interaction with graphical elements may occur in a variety of ways. For example, the provider GUI may provide information responsive receiving user interaction (e.g., selection) from the provider 112 through their associated client device. There are a wide variety of ways the system may receive user input, examples of which include but are not limited to: hovering over a graphical element with a pointer device or finger, holding a graphical element for a length of time, touching or clicking a graphical element one or more times. Additionally, information may be presented responsive to some constituent piece of information that the dashboard is able to present changes. The providing of information Responsive to being opened, the application 115 may generate a dashboard 300 including a navigation menu with various interactive elements. These may include a search tool so that a healthcare provider 112 may identify and be presented with information through other graphical elements regarding particular patients 111. The navigation menu may also include a notification menu including an identification for a new provider 112 or notifications the system also provided to patients 111, for example through cards. Finally, for security, the navigation menu may include a menu for regulating a provider's profile settings including updating passwords and logging in and out of the application 115 and dashboard 300.

IV.B. Patient Type Display

Figure 4A:
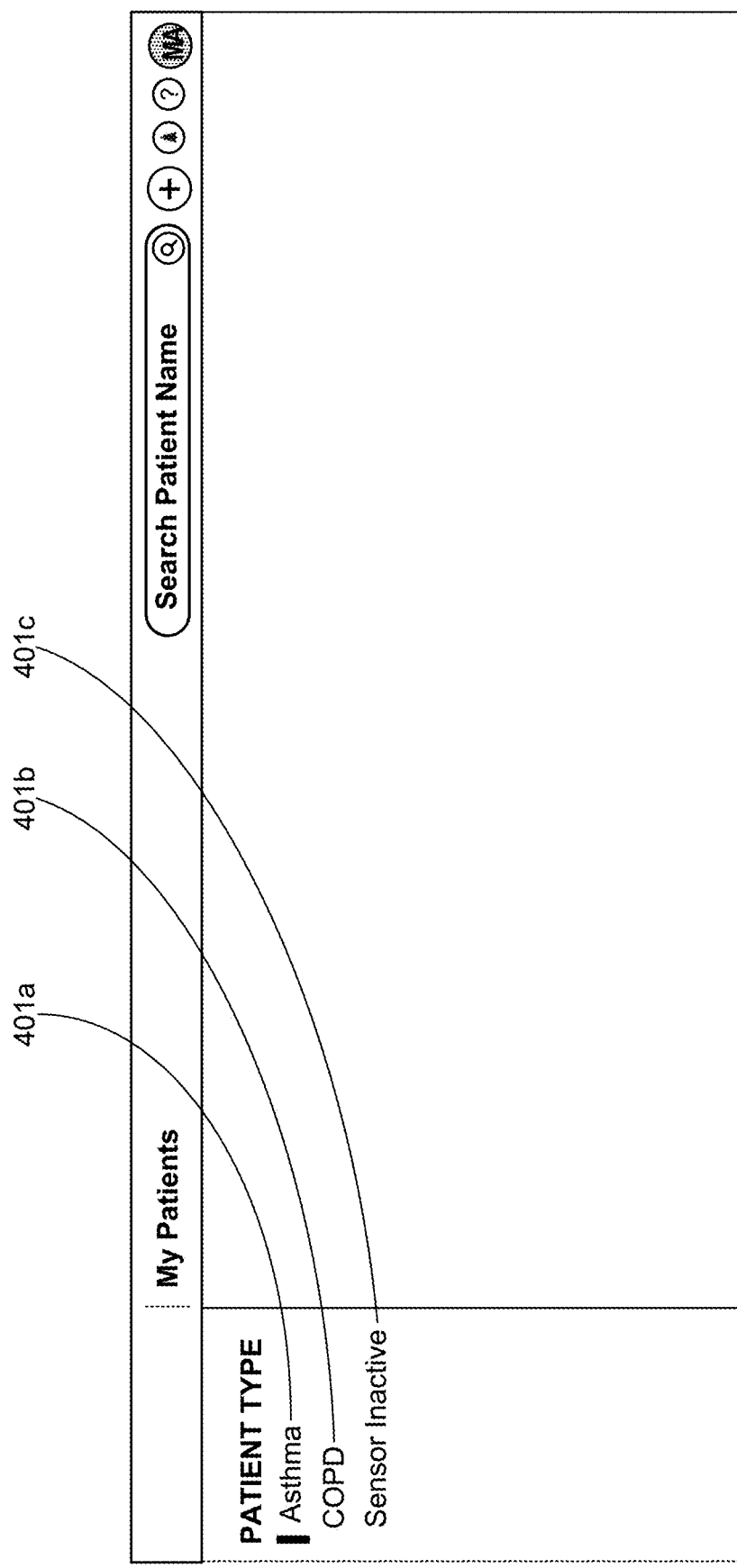

The patient type display 401 includes a visual menu of patient types that categorize the patients 111 for whom the provider 112 has authorization to monitor. Example patient types may include, but are not limited to, patients suffering from asthma 401a, patients suffering from COPD 401b, patients with cystic fibrosis (not shown), and patients with any other respiratory disease. Additionally, a separate entry in the menu may include patients with any of the diseases above but whose sensors are inactive 401c. The definition of inactive is described further below in Section IV.C Selecting any one patient type from the patient type display 401 causes the application 115 to generate a patient overview display 402 detailing a list of patients with that disease/device status along with information related to that status. FIG. 4A illustrates an example patient type display 401, according to one embodiment In some embodiments, the patient type display 401 may be displayed to the provider 112 upon selection of the patient list option from the navigation menu. Alternatively, it may be a default screen shown upon login.

IV.C. Patient Overview Display

The displayed content of the patient overview display 402 varies depending on the selected patient type.

FIG. 4B illustrates an example patient overview display 402 for an asthma patient type, according to one embodiment. Receipt of selection of the asthma patient type 401a causes the application 115 to display the patient overview display which includes a list of patients organized by name and including, for each patient, one or more of the following items of information related to the patients' management of their asthma: an asthma control score 402a, a report of rescue inhaler usage 402b, a report of controller inhaler usage 402c, a record of the most recent synchronization of a patient's client device 110 to an associated rescue medication sensor 402d associated with their rescue medicament device 160, a record of the most recent synchronization of the same or a different client device 110 to a controller sensor associated with their controller medicament device 160 (not shown), and a record of the most recent contact 402e between the patient 111 and the provider 112. Each of these items will be described in the following paragraphs in this section.

The asthma control score 402a is a derived rating that represents an estimate of the degree to which a patient has their asthma under control over a defined period time (e.g., 7 days, 1 month). The rating may be calculated and/or represented as a numerical score (e.g., a rating of 1-10, 1 being the low and 10 being the high) that is determined based on a patient's rescue inhaler and controller inhaler usage data, as reported by the sensors 120 associated with their medicament devices that are linked to the system 100. The asthma control score 402a may also be calculated or converted into a descriptive rating (e.g., very poor, not well, or well) that is easier to represent visually and more useful to the provider 112 when assessing many patients' statuses presented within the same graphical element. Further details regarding the calculation of the asthma control score 402a are described with respect to U.S. patent application Ser. No. 15/724,968, the contents of which are incorporated by reference herein.

The report of rescue inhaler usage 402b may be represented graphically on a per day basis with separate indicators for each day over a defined period of time, also referred to as a monitoring period. The monitoring period may be the same or different from the period of time used to determine the asthma control score 402a. In one embodiment, the report of rescue inhaler usage 402b is represented as a graphic illustrating each day within the period with a count of the total number of rescue events experienced during that day. In addition, the report 402b may include a cumulative account of the number of rescue events experienced during the period.

The report of controller inhaler usage 402c, also referred to as an adherence measurement, may be represented as a graphical indicator that visually indicates the patient's adherence over the same or a different monitoring period, in some embodiments along with printed characters indicating the adherence measurement The adherence measurement is determined based on the controller medication plan established by the patient 111 or the provider 112. In one embodiment, the adherence measurement represents a ratio of the amount of controller medication doses taken by the patient compared to the number of doses prescribed by the established controller medication plan, however in other embodiments the adherence measurement may be determined according to some other function incorporating information about controller medication doses taken and planned for. The adherence rating statistic 402c and the fillable graphic indicator are correlated, for example the fillable graphical indicator for a patient with a 64% adherence rating would only be 64% filled. The presented adherence measure and graphical element may be configured to record adherence measurements above 100% due to excessive controller inhaler usage by the patient. The fillable indicator in this instance could be filled to its maximum or otherwise graphically altered to indicate usage above 100% of adherence.

The adherence synchronization records 402d are represented visually as a date describing the last time a connection (e.g., BTLE) was established between the client 110 device and the rescue sensor 120 associated with the rescue medicament device 160. Synchronization itself generally occurs automatically, and it may also occur affirmatively in response to action by a user of the system communicating with or through a client device 110 accessing the system 100. In some cases, synchronization occurs in response to a change in triggering conditions or a detected rescue usage event. A failure to synchronize the rescue sensor with the patient's client device 110 may be due to a dysfunctional sensor or due to nonexistent or weak connection with the sensor. Similar to the rescue synchronization records 402d, the controller adherence synchronization records (not shown) may also represented visually as a date describing the last time a connection was established between a client device 110 and the controller sensor 120 associated with the controller medicament device 160. The same synchronization considerations described above apply to the controller adherence synchronization records.

The record of the most recent contact 402e between the patient 111 and the provider 112 is similarly updated based on communication records (e.g., phone, in-person, and/or electronic medical records (EMR)) of the patient and/or provider. The most recent contact 402e may also be updated based on notifications or other communications exchanged between the client devices 110 of the patient 111 and the provider 112 facilitated through the system 100, for example in the form of cards sent to and responded to by the patient 111, where the cards are sent based on manual actions taken by the provider 112 through actions processed using the dashboard 300.

As a means of maintaining patient privacy and consistency with HIPAA regulations, the patient overview display 402 includes a button 402f which can, responsive to user input, hide the list of patient names. Additionally, user input to the item of information 402a-402e sorts the patients based on the selected information. For example, in response to the selection of the asthma control score 402a, the list of patients may be reorganized in order of ascending scores. Additionally, in some implementations, providers may bookmark specific patients from the patient lists using a bookmarking feature 402g.

FIG. 4C illustrates another patient overview display 403 for a COPD patient type, according to one embodiment. Receipt of selection of the COPD patient type 401b causes the application 115 to generate a patient overview display a list of patients organized by name and including, for each patient, one or more of the following items of information related to those patient's management of their COPD: a rescue baseline assessment 403a, a report of rescue inhaler usage 403b, a report of controller inhaler usage 403c, a record 403d of the most recent synchronization of a patient's client device 110 to an associated rescue sensor 120, a record (not shown) of the most recent synchronization of the same or a different client device 110 to a controller sensor associated with their controller medicament device for each patient of the patient list, and a record of the most recent contact 403e between the patient 111 and the provider 112. Each of these items will be described in the following paragraphs of this section.

In one embodiment, the rescue baseline assessment 403a is determined based on a comparison between (1) an average number of daily rescue events determined over a baseline period of time with (2) the count of the rescue events for the current day. As with the previously described monitoring periods, the baseline time period may be established by the patient, the provider, the system, or by an authorized third party. In other embodiments, the rescue baseline may be determined according to any other function using items of information similar to those identified in the prior embodiment. The rescue baseline 403a may automatically updates whenever a rescue usage event is reported to the system by a patient's sensor 120 or client device 110.

The report of rescue inhaler usage 403b may be represented graphically on a per day basis with separate indicators for each day over a defined period of time, also referred to as a monitoring period. The monitoring period may be the same or different from the period of time used to determine the asthma control score 402a. In one embodiment, the report of rescue inhaler usage 402b is represented as a graphic illustrating each day within the period with a count of the total number of rescue events experienced during that day. In addition, the report 402b may include a cumulative account of the number of rescue events experienced during the period.

The report of rescue inhaler usage 403b may be described and represented graphically on a per day basis similarly to the representation described above in reference to the asthma patient overview display. Additionally, in some embodiments, the separate indicators may be color coded to characterize the number of rescue events for a given day. For example, the representation of the COPD patient overview display as shown in FIG. 4C, uses graphically differentiated indicators to represent days recording any number of rescue events (including zero), where different graphics are used to represent different numbers of rescue events. Days with no events (or alternatively days with events) may be particularly indicated as well.

The remaining patient data associated with the COPD patient type 401b, as listed above, is described and represented in ways consistent with their descriptions in reference to the asthma patient type 401a.

Receipt of selection of the sensor inactive patient type 401c causes the application 115 to generate a different patient overview display of a list of patients that includes, for each listed patient, one or more of the following factors: the period of time since the patient's client device was last synchronized with one of the patient's corresponding sensors (either rescue, controller, or otherwise), a period of time since the last recording of an event Thresholds for determining which patients are relevant for inclusion in this list may vary by implementation, and may be set statically or dynamically, and may further be set by the system operators, patients, providers, or authorized third parties. Any given patient may be listed if their rescue sensor 120 is not synched even if their controller sensor is synched, and vice versa. If the patient and their associated device/s meet multiple of the above factors for inclusion in this list, the second graphical element may selectively display the factor relevant to the most recent report of information from the patient 111 or sensor 120, depending on which is most recent in time.

IV.D. Patient Disease Management Display

As discussed above, the application 115 displays a patient overview display 402 with patient information in response to a selection of the patient type 401a received from a client device 110. While the patient overview display 402 is displaying this patient-related information, the patient overview display 402 and application 115, more generally, are configured to receive a selection input regarding a single one of the listed patients that the patient overview display 402 is displaying.

Figure 4D:
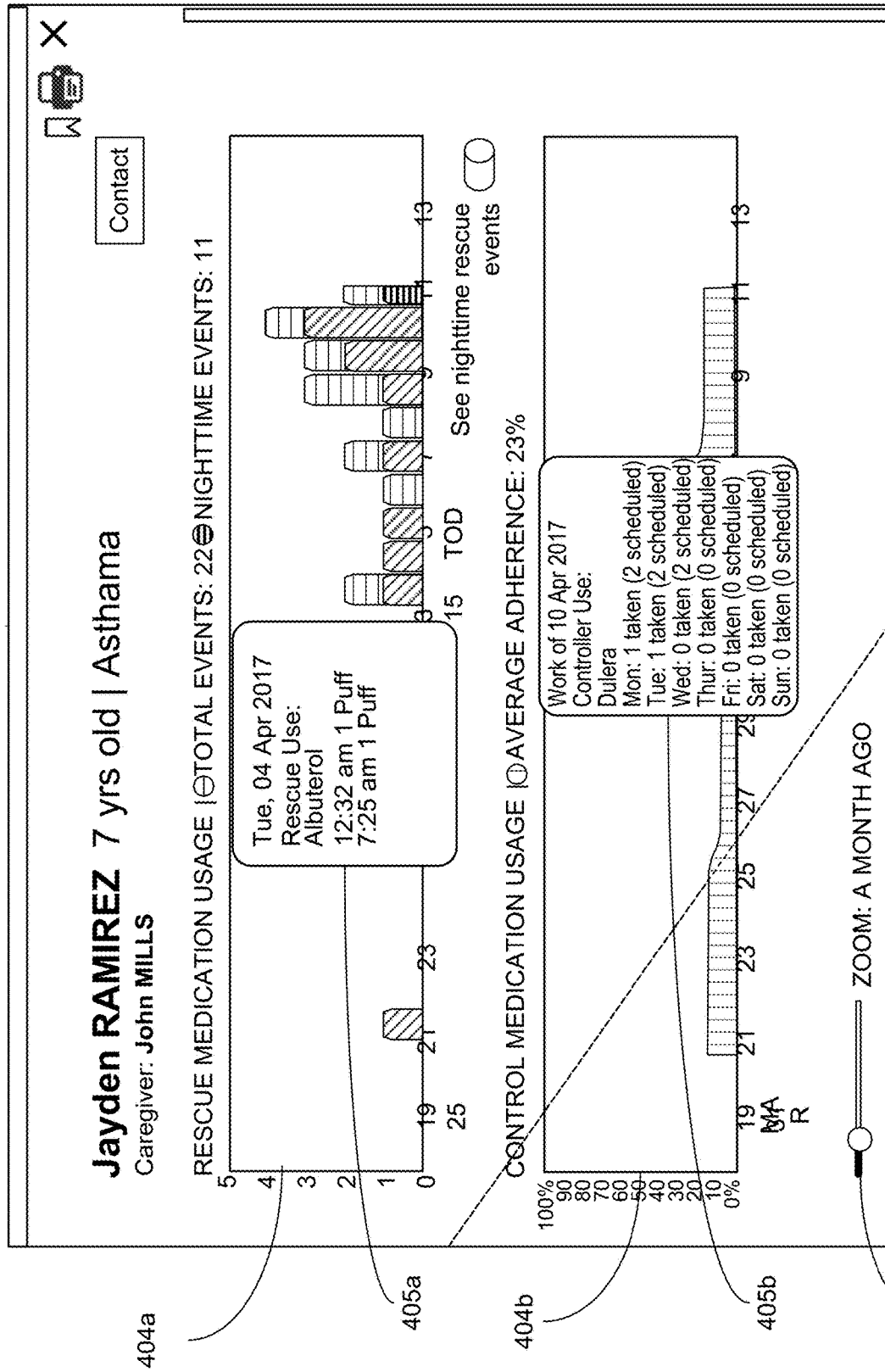

In response to the selection, the application 115 displays a patient disease management display 404 visually illustrating one or more of a history of reported rescue medication usage events 404a and a history of controller medication usage events 404b. FIG. 4D illustrates an example patient disease management display 404 for an example patient having the asthma patient type, according to one embodiment. The patient disease management display 404 may be displayed by the application 115 so that it is at least partially overlaying the patient overview display 402. The history of reported rescue medication usage events 404a and the history of controller medication usage events 404b are displayed at least as separate graphical, non-text elements diagramming the number of rescue or controller events as a function of time. These graphical event histories may be displayed concurrently with each other. The graphical histories may also overlap with each other (not shown). In the example embodiment of FIG. 4D, the histories are displayed as histograms, however in alternate implementations any similar data plotting mechanism may be used, such as line plots.

Additionally, the patient disease management display 404 includes a selectable element 404c configured to receive a user input and, in response to the user input, adjusts the time frame of one or both of the graphical event histories. In the illustrated example embodiment of FIG. 4D, the selectable element 404c is represented as a sliding graphical indicator. The adjustment of the time frame of the graphical histories may be implemented by expanding the range of dates to include events beyond a given point in time or by shrinking the range of dates to exclude events beyond a given point in time. Either of these may be accomplished by changing the dates of events considered forward and/or backward in time accordingly. The expansion or contraction of dates considered may be symmetric with respect to some "center" date, or the selectable element may include sub elements allowing input to custom configure the date range. Within the graphical event histories, individual bars indicate the number of rescue events or the adherence rating of the patient 111 on a specific day.

IV.E. Patient Daily Rescue Display

While the patient disease management display is displaying the graphical event histories, the application 115 is configured to receive a selection input regarding a single day from the graphical history of reported rescue medication usage events 404a or the graphical history of controller medication usage events 404b. In response to the selection, the application 115 generates a patient daily display related to the selected graphical event history. Selection of a single day from the history of rescue medication usage results in the application 115 displaying a patient daily rescue display 405a, whereas selection of a single day from the history of controller medication usage events 404b causes the application 115 to display a patient weekly controller display 405b. The patient daily display may at least partially overlay the patient disease management display 404. In some embodiments, responsive to a receipt of user input to the patient daily displays, the application 115 may generate patient daily displays 404 that significantly if not completely overlay the patient disease management display 402. The patient daily displays are displayed as text boxes containing verbal information regarding a patient's rescue or controller medication trends, however in alternate embodiments any similar presentation format may be used. Although this paragraph describes a daily view specifically, in practice, inputs may result in views covering other periods of time as well, such as half-days, hours, and so on.

Figure 4E:
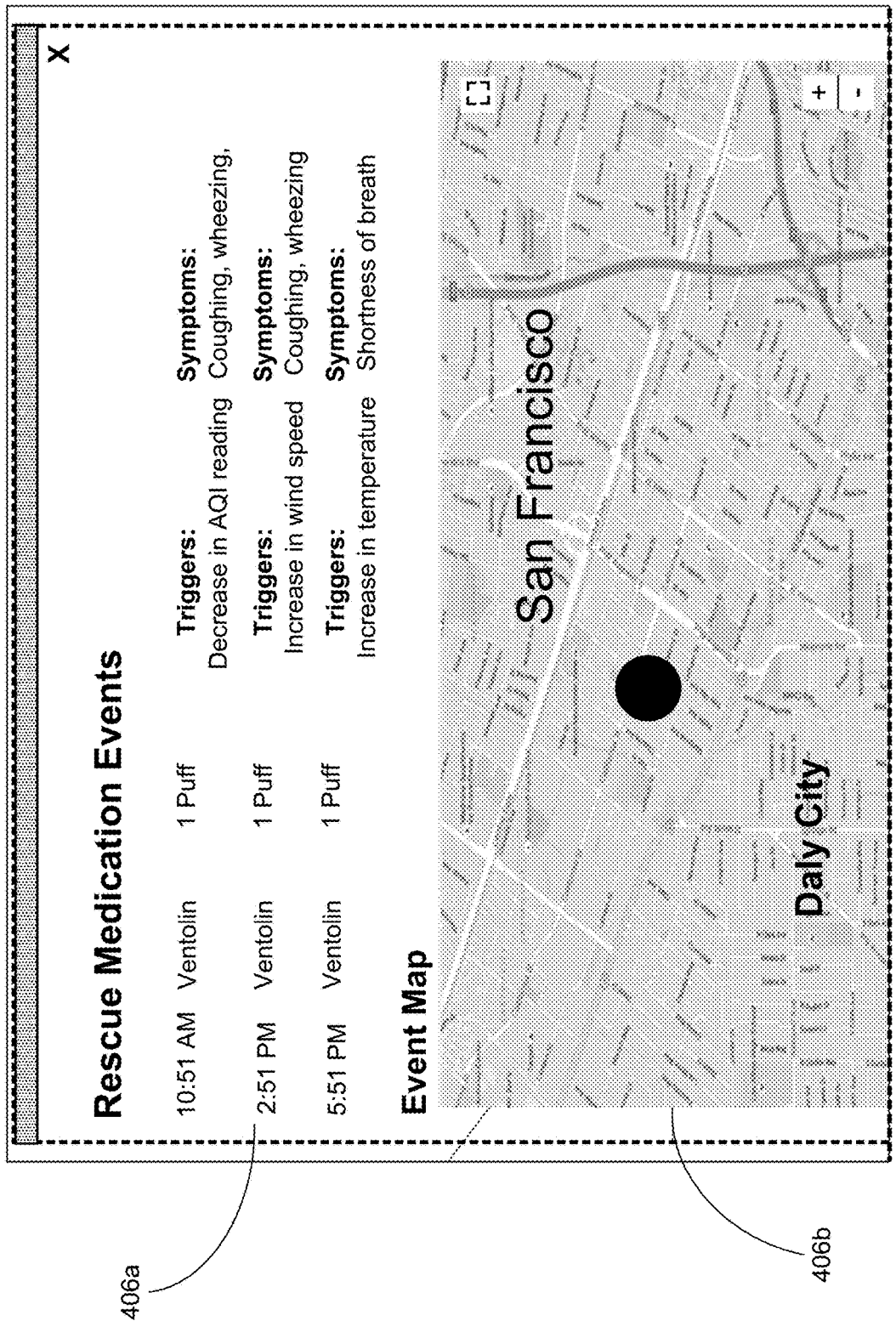

The patient daily rescue display includes one or more of the following: the name of the rescue medication used during the rescue event, the dosage of that medication, and the time at which the dosage was expensed, and whether the rescue event was detected by the rescue sensor 120 or recorded manually by a user. For example, in the illustrated embodiment of FIG. 4D, the patient daily rescue display 405a reports that Albuterol was used during two events and for each event a dosage of a single puff was used An alternate embodiment of the patient daily rescue display 406 is shown in FIG. 4E. In addition to the information presented in FIG. 4D, the patient daily rescue display may also present information 406a regarding any triggering conditions or symptoms experienced by the patient. Triggering conditions may be environmental (e.g., air quality index, humidity, temperature, wind speed, etc.) or habitual (e.g., missed controller medication doses). In addition to the triggering conditions and symptoms, the patient daily rescue display may comprise a geographical map 406b detailing the locations of the rescue medication usage events. In some embodiments, the geographical map 406b may include a second selectable element configured to receive a user input, and in response to the user input, incrementally adjust the level of visual detail for the map.

In the embodiment illustrated by FIG. 4E, the selectable elements is represented as two buttons. The adjustments may be implemented by expanding the field of view beyond a given point on the map to include more high level information (e.g. city names, surrounding landforms) or minimizing the field of view to include more low-level information (e.g., street names, specific addresses). The expansion and minimization mechanics for the geographical map 406b are consistent with those described earlier in reference to the selectable element 404c displayed in FIG. 4D.

IV.F. Patient Weekly Controller Display

Similar to the patient daily rescue display, responsive to receipt of a selection of a single day or a range of days from the history of controller medication usage, the application 115 displays a patient weekly controller display at least partially overlaying the patient disease management display. The patient weekly controller display includes one or more of the following: the name of the controller medication used during the selected dates and a record of medication doses taken versus medication does recommended for each day during the selected dates. For example, in the embodiment illustrated in FIG. 4D, the patient weekly controller display reports that on Monday the patient took one dose of Dulera out of the recommended two doses.

An alternate view of the patient weekly controller display 407 is shown in FIG. 4F. In addition to the information provided in FIG. 4D, the alternate fourth graphical element 407 may include details 407a regarding the medicament device (e.g., the synchronized client device, a dosage schedule for the patient, and the recommended dosage for the medication). Additionally, the fourth graphical element 407 may include further details 407b regarding day to day controller medication activity, such as the medication taken and the time that the medication was taken.

IV.G. Patient Summary Display

Figure 4G:
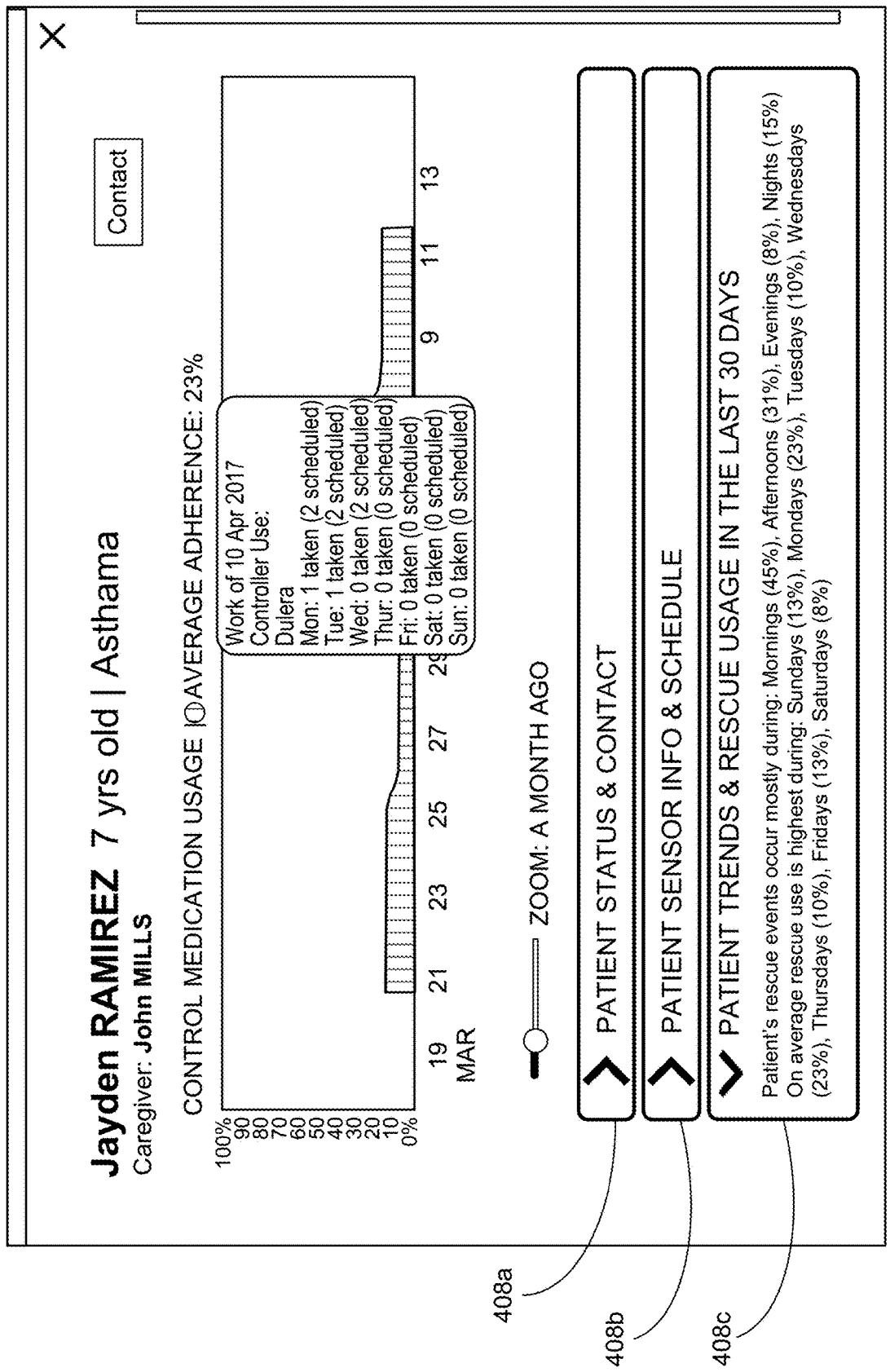

The patient disease management display 404 also may include a scrollable element, which in response to user input reveals a patient summary trend display as illustrated in FIG. 4G. The patient summary trend display includes one or more of the following: a patient status tab 408a, a patient sensor info tab 408b, and a 30 day patient trends tab 408c. In some implementations, these tabs may be selectable, responding to user selection by revealing or hiding additional information. The 30 day patient trends tab 408c may include details regarding a breakdown by percentage of when a patient's rescue events occur (e.g., mornings, afternoons, evenings, or nights) and a breakdown by percentage of a patient's rescue usage per day. In other implementations, this data may be represented graphically or visually or include additional trend details.

V. Patient Side Graphics Display

As described previously in reference to the dashboard 300, in some embodiments patient 111 client devices 110 may be sent notifications regarding environmental conditions, medication regimens, or their personal health using any one of a variety of different display cards which may be organized into categories.

An information card type includes cards that display data. Information cards may, for example, display medication rescue events, statistics, and maps including both patient data and community data. Information cards are further sub-categorized into event, trend, education, and alert display cards.

Figure 5A:
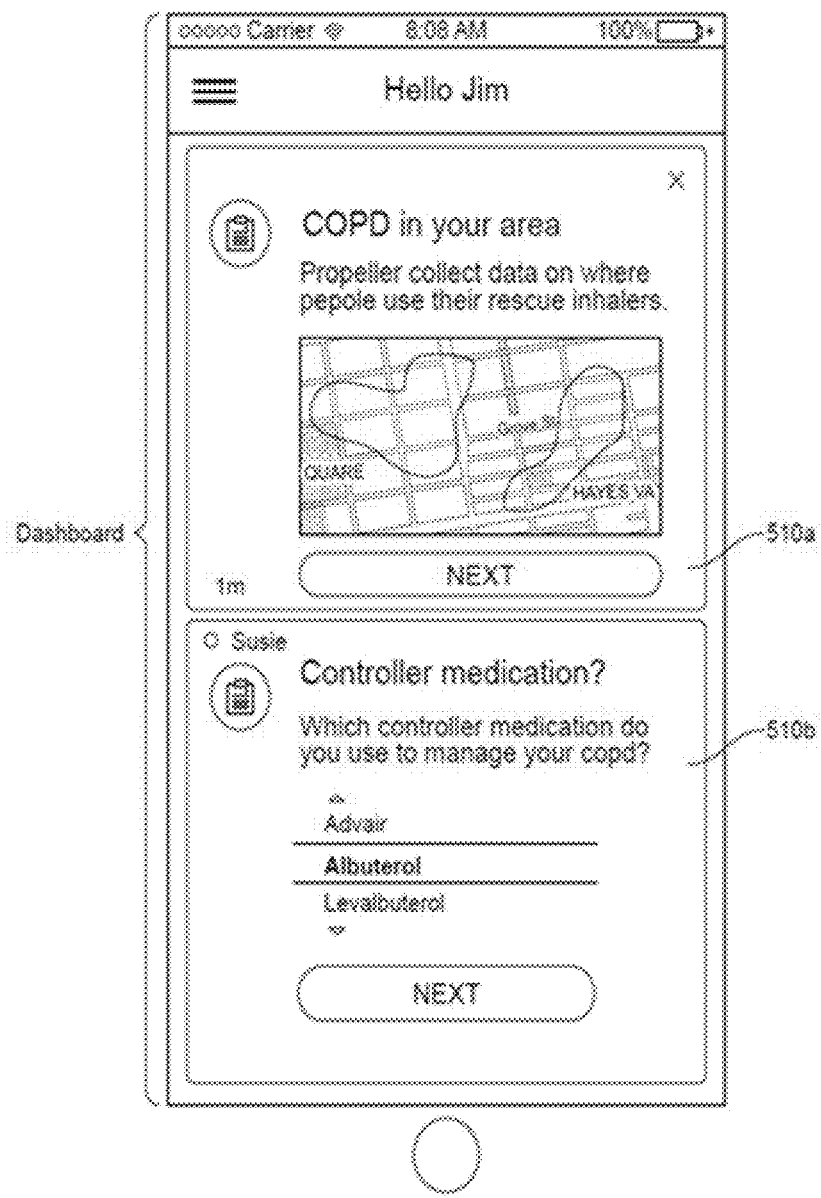
Figure 5B:
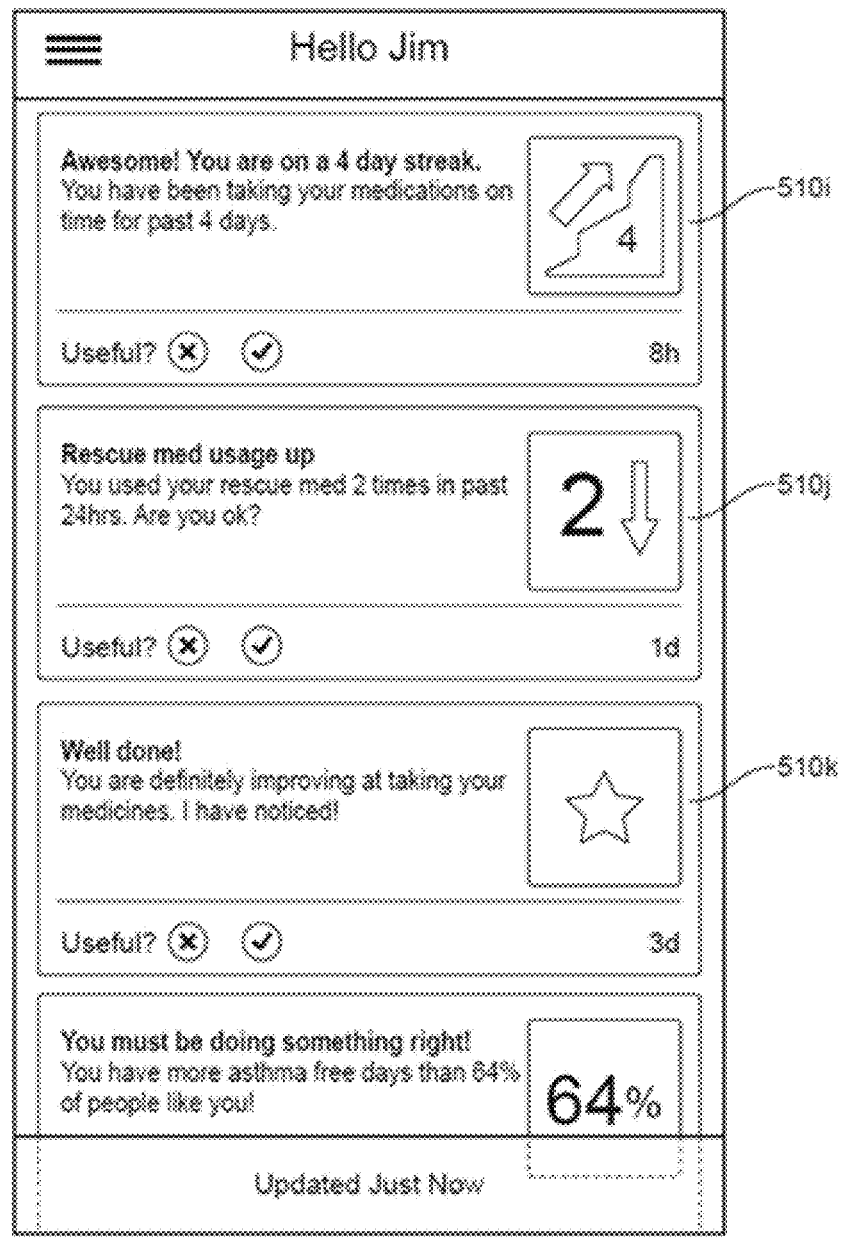
Figure 5C:
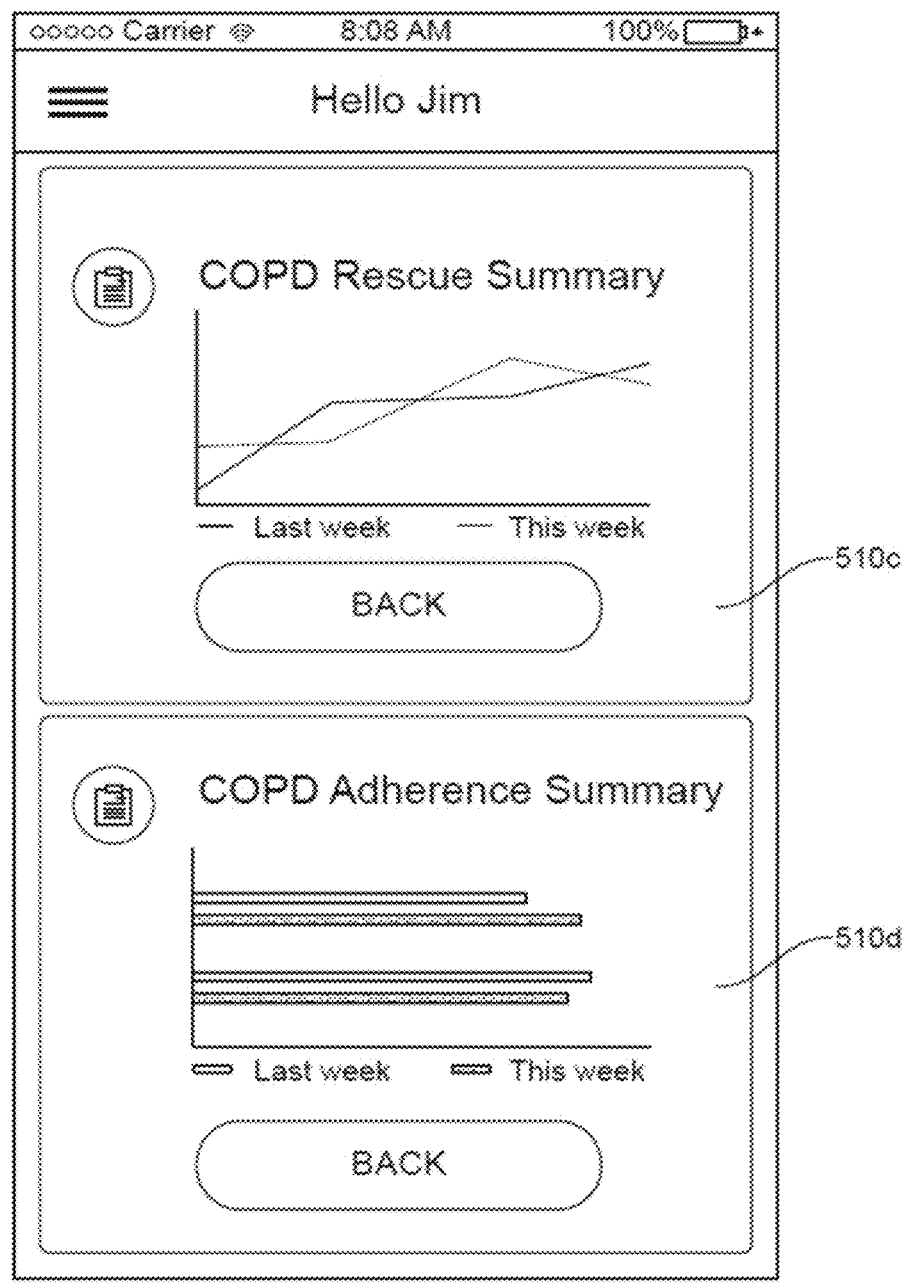
Figure 5D:
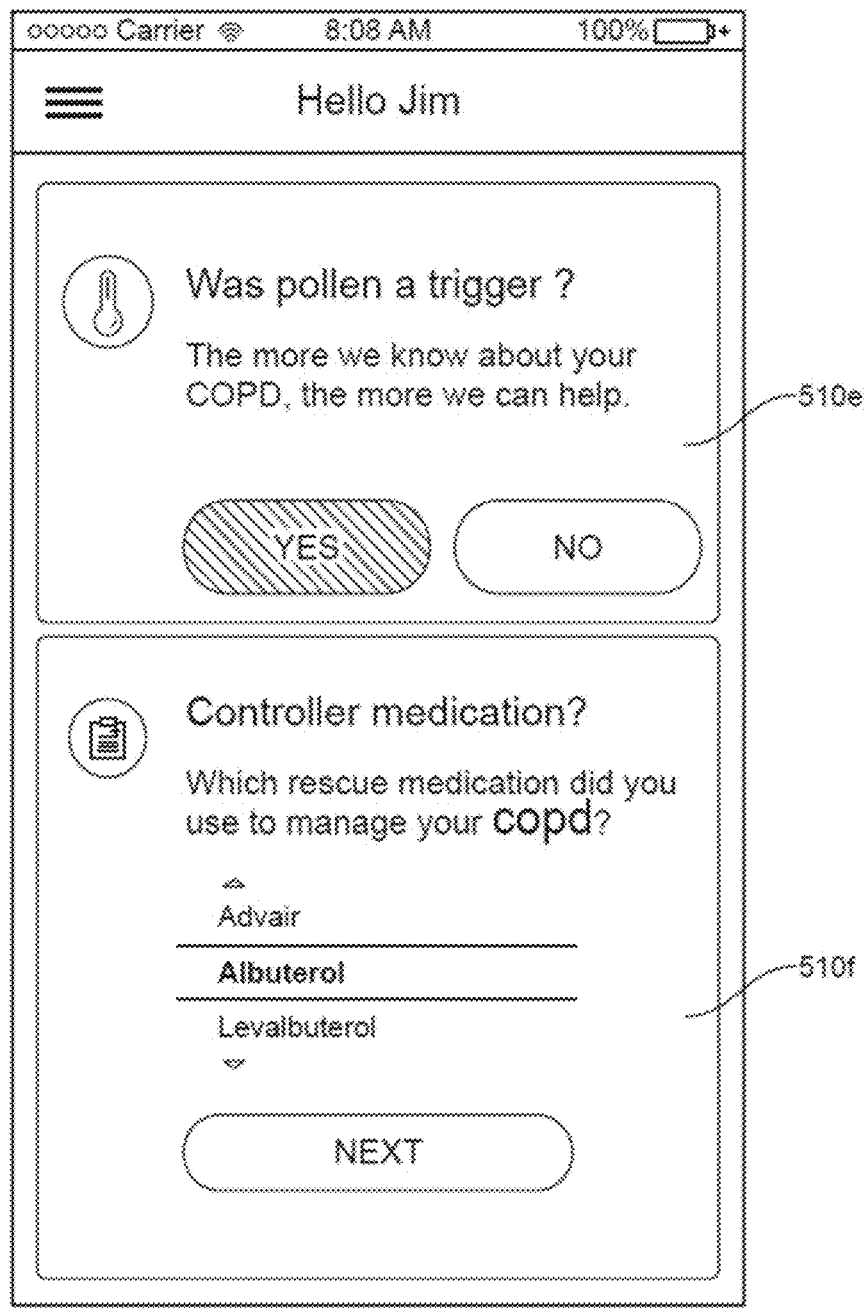
Figure 5E:
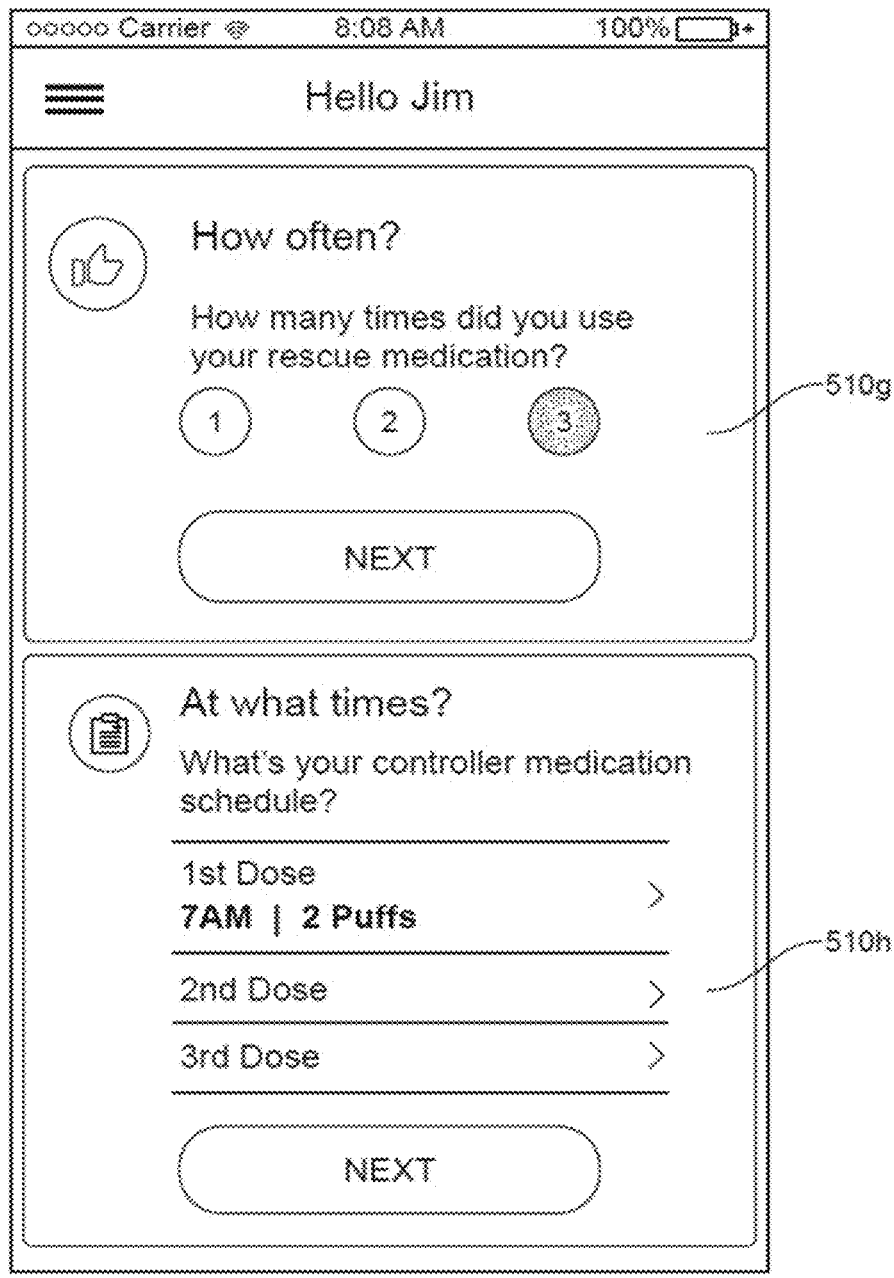
Figure 5F:
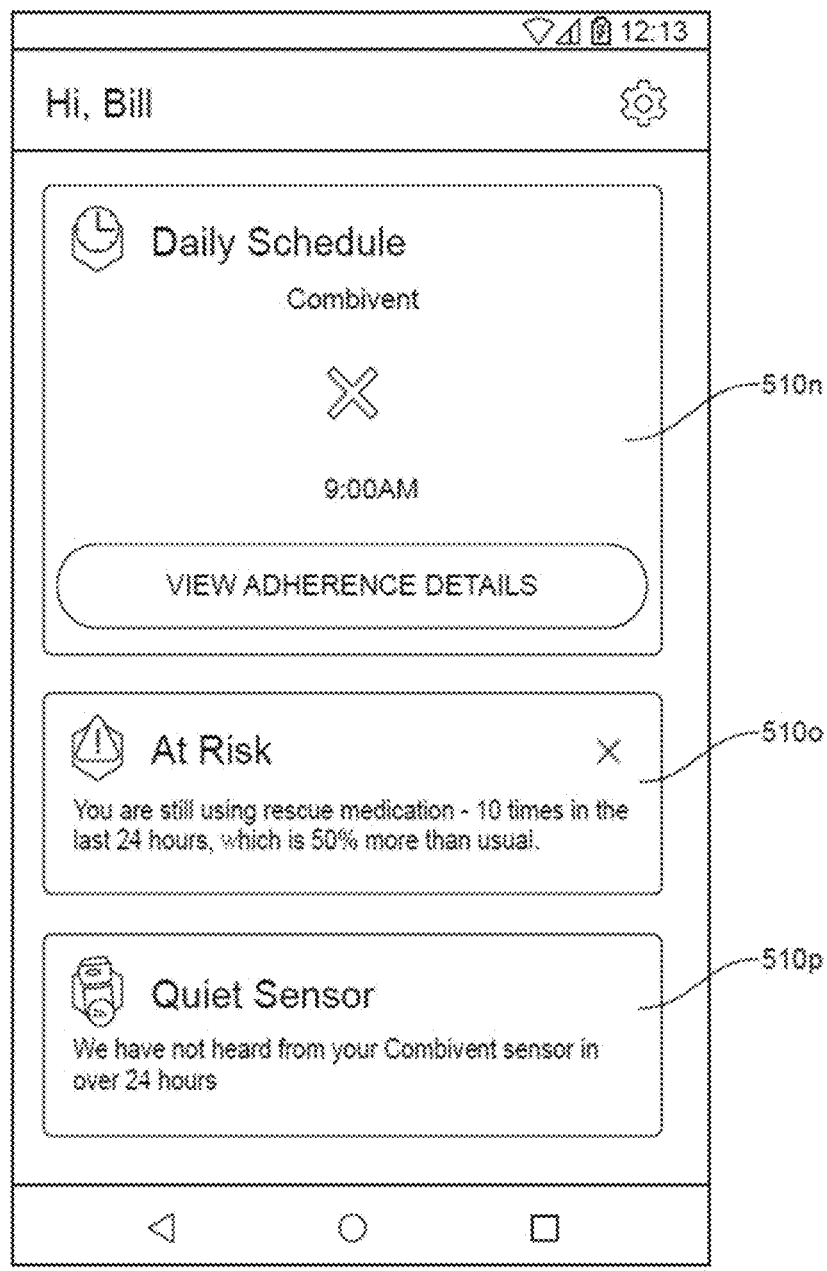
Figure 5G:
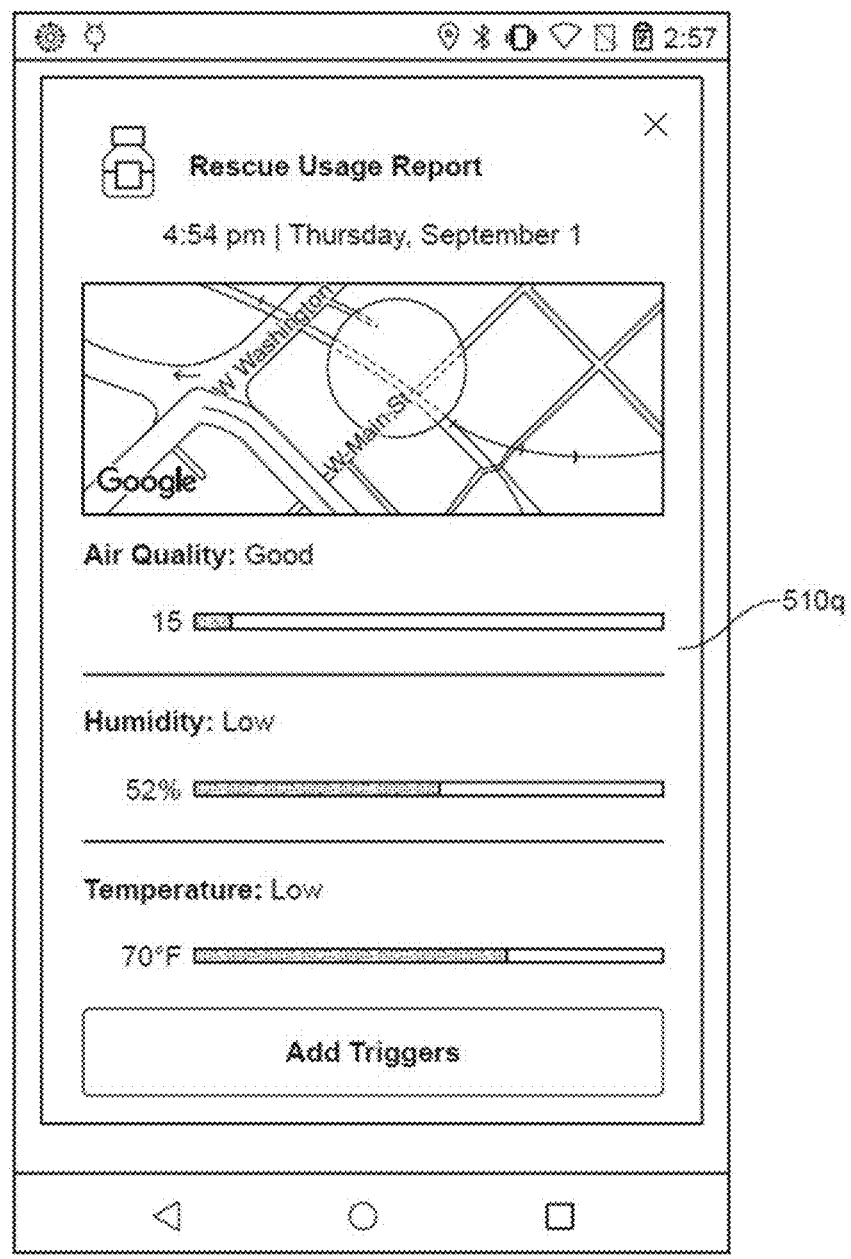
Figure 5H:

Event cards include data relating to rescue medication events, such as a list of historical medication rescue events for a specific patient, or patient rescue event data overlaid on a geographical map for a specific provider. For example, the display card 510a illustrated in FIG. 5A is an event card that highlights patients experiencing asthma rescue events in a particular geographic area. The display card 510q illustrated in FIG. 5G is an event card that displays an example medication usage report. The example medication usage report includes a map of location of a rescue usage event, environmental conditions at the location, and an input response area 315 for the recipient to add triggers for the rescue usage event.

Figure 5I:
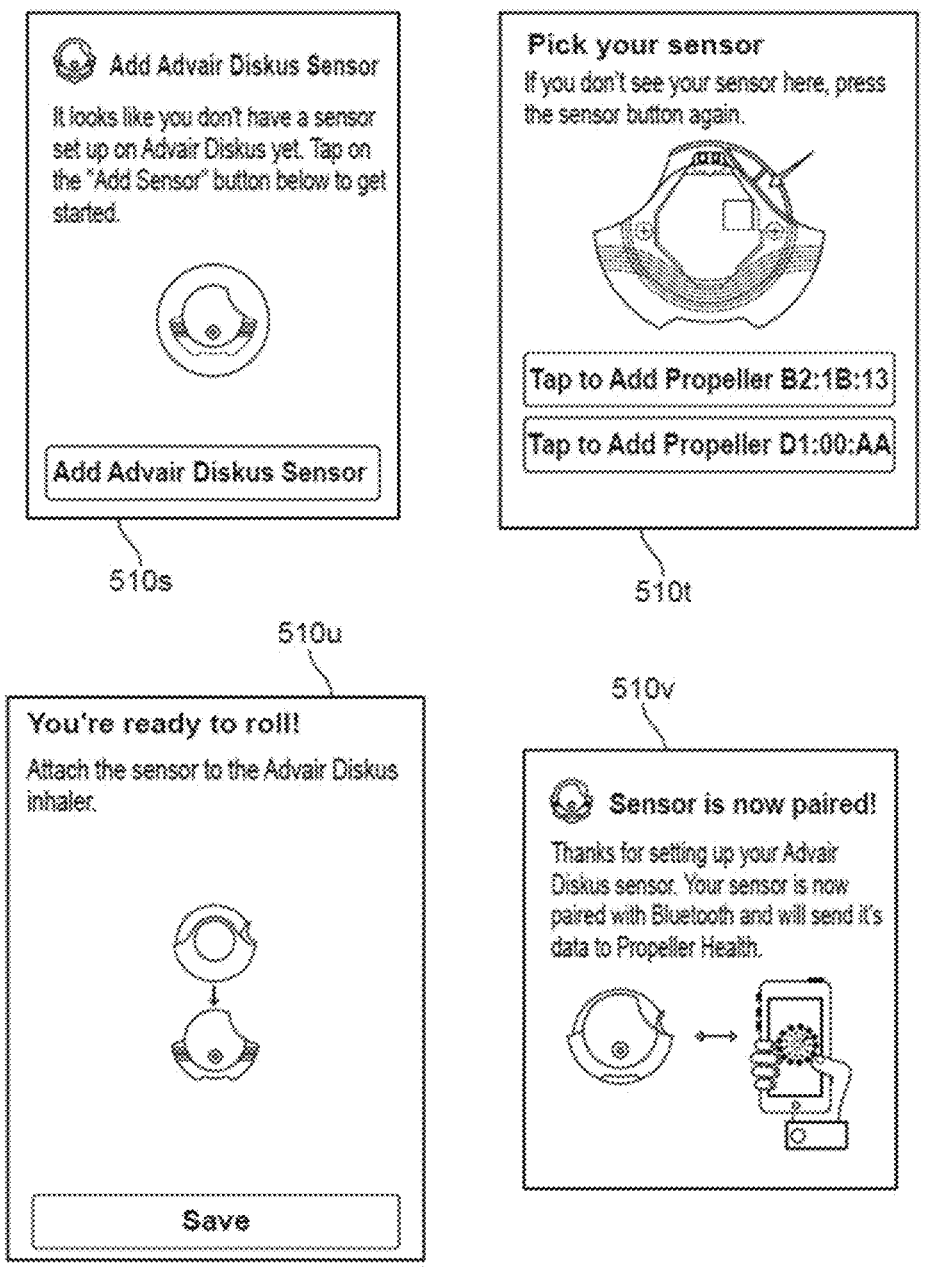
Figure 5J:
Figure 5K:
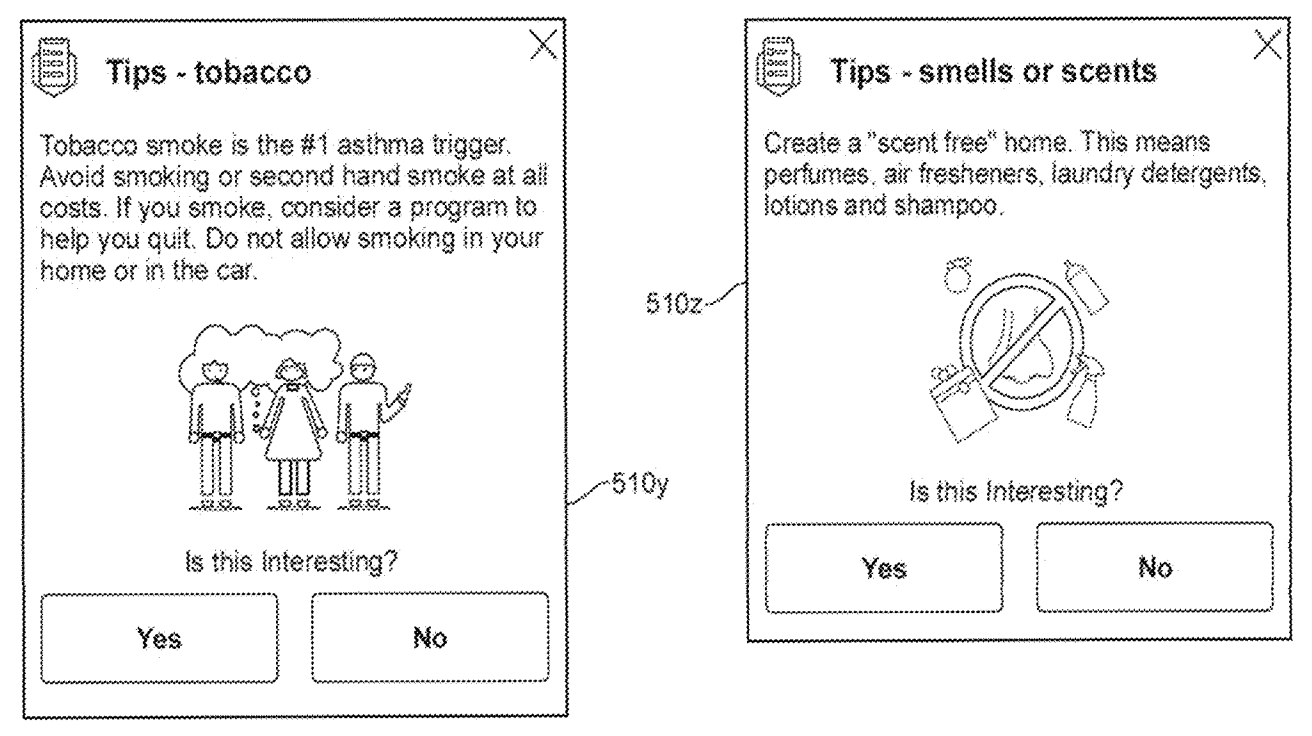
Figure 5L:
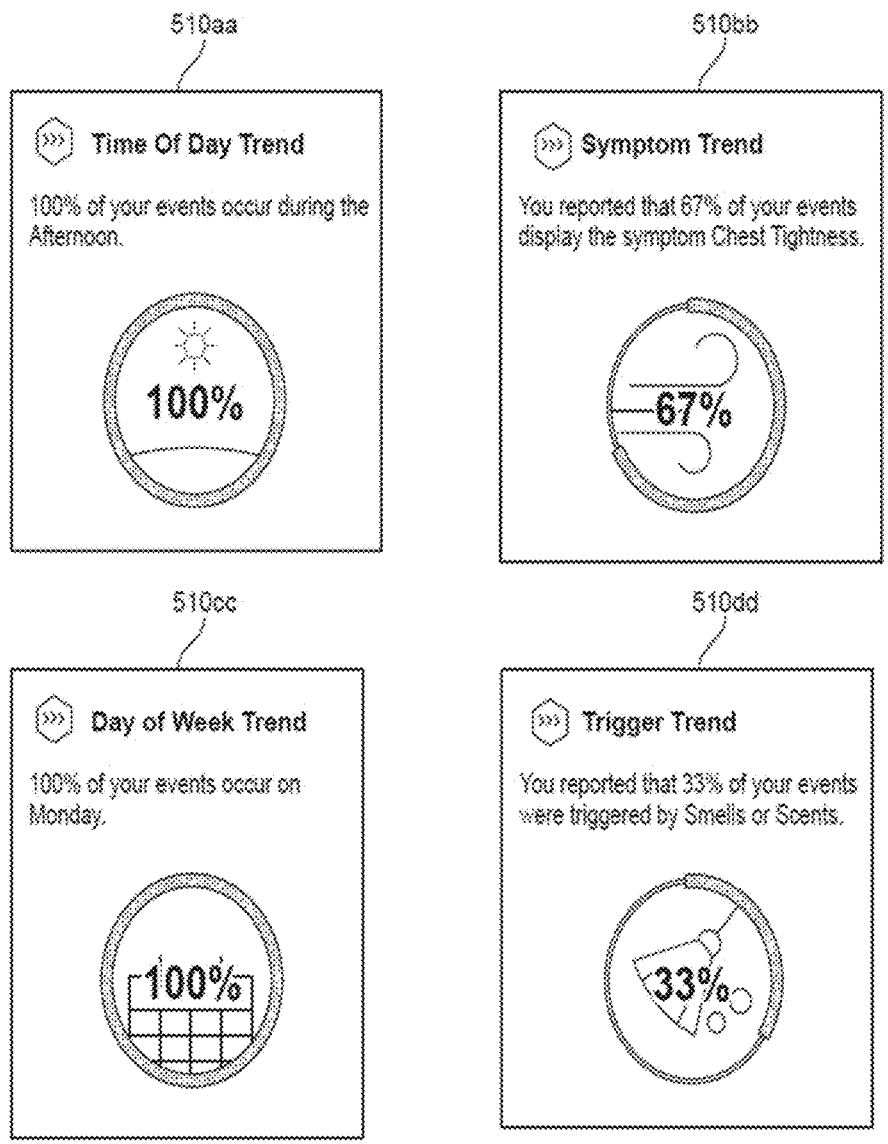

A trend card includes statistical information presented using a graph or a chart designed for clear comprehension by the recipient. FIG. 5C illustrates two different example trend cards, plotting asthma rescue events 510c and asthma controller medication adherence 510d, both over various time periods. FIG. 5L illustrates four different example trend cards. Card 510aa displays a time of day trend, card 510bb displays a symptom trend, card 510cc displays a day of week trend, and card 510dd displays a trigger trend.

An education card includes information meant to educate the recipient. FIGS. 5J and 5K illustrate education cards, providing general disease information 510w and 510x and providing tips for recipients 510y and 510z. Education cards may include an input response 315 to allow recipients to specify whether the information provided is relevant or interesting for use in serving future cards.

Figure 5M:
Figure 5M:
Figure 5M:

Alert cards notify users of important information. Cards 510o and 510p of FIG. 5F are alert cards for informing a recipient that they are at risk for an event 510o and that data has not been received from a device over a recent time period 510p. FIG. 5M illustrates example alert cards. Card 510ee is similar to card 510o and card 510f is similar to card 510p. Card 510gg informs a recipient that a particular dose of medication has not been recorded by a device. Other alerts may include an alert that a setting on the client device is preventing syncing (e.g., BLUETOOTH is turned off) or that a patient's Asthma Control Test score has changed.

A survey card type solicits a user response by presenting yes/no, multiple choice, or more open-ended questions for the user to respond to. For example, a healthcare provider or the analytics system 100 may send a survey card with a COPD, asthma, or other questionnaire to a patient 111 to determine a level of disease control for a specific patient. As an additional example, a survey card may request the type of controller medication that the patient 111 uses to treat asthma symptoms, as shown in the display card 510b illustrated in FIG. 5A. Generally, survey cards provide the application server 130 with data that may be missing from a patient's medical history or patient profile (as introduced above), and/or provide an update to possible outdated information. Generally, one or more survey cards may be used to complete the patient enrollment process and create a patient profile for storage in database server 140. As a specific example, when a patient 111 initially enrolls in the analytics system 100, a push notification will be triggered by the application server 130 prompting the patient 111 to create a patient profile. Example of survey cards are illustrated in FIGS. 5D and 5E, which illustrates a survey question asking whether a patient has made an emergency room visits as a result of asthma exacerbations, what the patient's controller medication is 510f, how many times the patient used their rescue medication to control an event 510g, and what their controller medication daily schedule is 510h. Survey cards may also ask about a patients asthma triggers, such as whether pollen is a trigger 510e. Other survey cards ask a patient to rate their general quality of life on 5-point Likert scale, to rate their quality of sleep, to rate their ability to be active over last 7 days, and so on. Other survey cards ask whether the patient feels better or worse than yesterday, whether the patient has had to go to emergency room or hospital in last 12 months for an exacerbation and so on.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient is currently using as listed on their medicament device 160, in order to verify that the correct medication is being used. As another example, if the reported information about controller medication use indicates that the patient is only using the controller medication one time per day but their adherence plan indicates they are supposed to be taking their controller medication twice per day, system 100 could send a notification asking if the patient needs to change their adherence plan.

Navigation cards represent actionable data or messages that, upon user interaction, may redirect the user to another screen or card that is part of the dashboard 300. For example, if a patient wants to share information or request specific medication plans for controller medications with a physician, a navigation card would be used to facilitate the sharing of information or enrollment in controller adherence plan. Additionally, navigation cards allow users to update information surrounding medication rescue events.

Adherence cards are designed to encourage a patient to continually use their controller medication on schedule over different periods of time. FIGS. 5B, 5C, and 5F illustrate example adherence cards. Cards 510i illustrates an example of a "streak" or continuous run of on-time controller medication events, card 510k illustrates better performance in aggregate even if no streak has been achieved, and card 510 presents improved patient health with respect to the number of asthma symptom-free days experienced. Card 510j is a survey card that inquires as to the patient's physical state in response to recording a significant number (e.g., two) rescue medication events within a threshold period of time of each other (e.g., 24 hours). Card 510m illustrates controller medication events as a graph, illustrating when the patient 111 did and did not take their controller medication on time during various periods during the day, as prescribed by their health care provider 112. Card 510n illustrates a daily schedule for controller medication and an indicator for displaying whether the scheduled dose has been taken. In the example of card 510n, the indicator is a red "X" indicating the scheduled dose has not been taken. A green check mark or another symbol could be used to indicate that the scheduled does has been taken.

Setup cards guide recipients in associating sensors with client devices 110. FIG. 5I illustrates example setup cards for pairing a sensor to a client device 110 using BLUETOOTH. Card 510s prompts the recipient to initiate the pairing process. Card 510t prompts the user to select a sensor device for pairing. Cards 510u and 510v notify the user that the sensor is paired.

In one implementation of FIG. 3, an example user interface presented in the dashboard 300 illustrates a medication list. The list includes medication information such as medication type (rescue, controller, etc.), dosage schedule, and sensors. Recipients may interact with the list to add, edit, and delete medications and medication information.

VI. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for displaying patient information on a display of a computing device associated with a healthcare provider, the method comprising:
for each patient of a plurality of patients,
receiving, at a remote server, a report of rescue inhaler usage for the patient over a time window, the report of rescue inhaler usage reported to the remote server by a first sensor mounted to a rescue inhaler to monitor activation of the rescue inhaler associated with the patient with a geographical location where each rescue inhaler usage event of the the report of rescue inhaler usage occurred, wherein the first sensor records the geographic location where each rescue inhaler usage event occurred and the remote server recognizes the report of rescue inhaler usage events based on a device identifier unique to the first sensor; and receiving, at the remote server, a report of controller inhaler usage for the patient over the time window, the report of controller inhaler usage reported to the remote server by a second sensor mounted to a controller inhaler to monitor activation of the controller inhaler associated with the patient with a geographical location where each controller inhaler usage event of the report of controller inhaler usage occurred, wherein the second sensor records the geographic location where each controller inhaler usage event occurred and the remote server recognizes the report of controller inhaler usage events based on a device identifier unique to the second sensor;

transmitting, for display on the computing device associated with the health care provider, a first graphical element identifying a plurality of patient types to the healthcare provider, each of the plurality of the patient types associated with a disease and one or more patients of the plurality of patients who have that disease;

responsive to receiving a selection by the health care provider, transmitting a second graphical element to be displayed on the computing device associated with the health care provider concurrently with the first graphical element, the second graphical element containing patient asthma monitoring information for one or more patients who have asthma, the patient asthma monitoring information comprising:
the report of rescue inhaler usage for each patient of the one or more patients who have asthma over the time window; and
the report of controller inhaler usage for each patient of the one or more patients who have asthma over the time window; and responsive to the health care provider selecting a patient from the one or more patients who have asthma and reviewing the report of rescue inhaler usage and the report of controller inhaler usage, generating a notification requesting updated medication information from the selected patient based on inputs from the provider; and
transmitting the notification to the selected patient.

2. The method of claim 1, wherein the health care provider selects an asthma patient type from the first graphical element by a user input, the user input comprising one or more of the following:
hovering over a graphical element representing the patient types;
holding a graphical element representing the patient types; or
touching a graphical element representing the patient types one or more times.

3. The method of claim 1, wherein the first graphical element displays a plurality of patient types to the health care provider, the plurality of patient types further comprising:
a chronic obstructive pulmonary disease (COPD) patient type; and
a sensor inactive patient type.

4. The method of claim 3, wherein an alternate second graphical element is displayed in response to a selection of the COPD patient type, the alternate second graphical element containing patient COPD information for one or more patients who have COPD, the patient COPD monitoring information comprising:

for each patient of the one or more patients who have COPD,
a rescue baseline assessment determined by comparing a number of rescue events reported over a time window to a threshold number of rescue events;
a report of a rescue inhaler usage over the time window; and
a report of a controller inhaler usage over the time window.

5. The method of claim 3, wherein an alternate second graphical element is displayed in response to a selection of the COPD patient type, the alternate second graphical element containing patient COPD monitoring information for one or more patients who have COPD, the patient COPD monitoring information comprising:
for each patient of the one or more patients who have COPD,
a record indicating a most recent synchronization of a first computing device associated with a first sensor coupled to a rescue inhaler associated with the patient; and
a record indicating a most recent synchronization of a second computing device associated with a second sensor coupled to a controller inhaler associated with the patient.

6. The method of claim 3, wherein an alternate second graphical element is displayed in response to a selection of the sensor inactive patient type, the sensor inactive patient type containing monitoring information for one more patients associated with an inactive sensor, the monitoring information comprising:
for each patient of the one or more patients associated with an inactive sensor,
a period of time since a first computing device associated with the patient was last synchronized with a sensor coupled to a rescue inhaler associated with the patient; and
a period of time since a second computing device associated with the patient was last synchronized with the sensor coupled to a controller inhaler associated with patient.

7. The method of claim 3, wherein an alternate second graphical element is displayed in response to a selection of the sensor inactive patient type, the sensor inactive patient type containing monitoring information for one more patients associated with an inactive sensor, the monitoring information comprising:
for each patient of the one or more patients associated with an inactive sensor,
a record that a period of time since a recording of a rescue inhaler usage event exceeds a first threshold period of time; and
a record that a period of time since a recording of a controller inhaler usage event exceeds a second threshold period of time.

8. The method of claim 1, wherein the second graphical element further comprises an asthma control score determined at the remote server, the asthma control score determined based on rescue inhaler usage data reported by the first sensor mounted to the rescue inhaler to monitor activation of the rescue inhaler and controller inhaler usage data reported by the second sensor mounted to the controller inhaler to monitor activation of the controller inhaler.

9. The method of claim 1, wherein the second graphical element further comprises a record indicating a most recent synchronization of a first computing device with a first sensor mounted to a rescue inhaler associated with each of the one or more patients who have asthma.

10. The method of claim 1, wherein the second graphical element further comprises a record indicating a most recent synchronization of a second computing device with a second sensor mounted to the controller inhaler associated with each of the one or more patients who have asthma.

11. The method of claim 1, wherein the second graphical element further comprises a record indicating a most recent contact between each patient of the one or more patients who have asthma and the health care provider.

12. The method of claim 1, wherein the report of rescue inhaler usage is represented over the time window on a per day basis, wherein each day during the time window displays a number of rescue events detected on that day.

13. The method of claim 1, wherein the report of controller inhaler usage is represented as a fillable graphical indicator for each patient of the one or more patients who have asthma, the fillable graphical indicator displaying a statistic determined based on a measure of the patient's adherence rating over the time window.

14. The method of claim 1, further comprising:
receiving an input to the second graphical element selecting patient asthma monitoring information for the patient from the one or more patients who have asthma; and
responsive to receiving the input, at least partially overlaying a third graphical element with the second graphical element, the third graphical element visually illustrating a history of rescue medication usage events reported by a first sensor mounted to a rescue inhaler associated with the selected patient and a history of controller medication usage events reported by second sensor mounted to a rescue inhaler associated with the selected patient.

15. The method of claim 14, wherein the history of rescue medication usage events and the history of controller medication usage events are displayed concurrently within the third graphical element.

16. The method of claim 14, wherein the third graphical element further comprises:
a sliding graphical indicator for adjusting the time window, wherein adjusting the time window manipulates a number of rescue medication usage events and a number of controller medication usage events displayed in the third graphical element.

17. The method of claim 16, wherein adjusting the time window comprises:
expanding the time window to include events reported before a certain time; or
shrinking the time period to events reported after the certain time.

18. The method of claim 14, wherein the history of rescue medication usage and history of controller medication usage are displayed as a sequence of histograms, wherein each histogram of the sequence of histograms represents a number of events reported during a day during the time window.

19. The method of claim 14, further comprising:
receiving an input to the third graphical element, the input selecting one of:
a single day with a reported rescue medication usage event; or
a single day with a reported controller medication event; and
responsive to receiving the input to the third graphical element, at least partially overlaying a fourth graphical element on the third graphical element, the fourth graphical element visually illustrating additional information regarding the selected single day.

20. The method of claim 19, wherein the input to the third graphical element selects a single day with a reported rescue medication usage event, the additional information comprising:
- a date of the reported rescue medication usage event;
- a rescue medication dispensed during the reported rescue medication usage event;
- a time of the reported rescue medication usage event; and
- a dosage of the dispensed rescue medication.

21. The method of claim 19, wherein the input to the third graphical element selects a single day with a reported controller medication usage event, the additional information comprising:
- a week when the controller medication usage event was reported;
- a controller medication dispensed during the reported controller medication usage event;
- a per day recording of recommended controller medication doses; and
- a per day recording of controller medication doses taken by the selected patient.

\* \* \* \* \*